United States Patent [19]

Ryer et al.

[11] Patent Number: 4,776,969

[45] Date of Patent: Oct. 11, 1988

[54] CYCLIC PHOSPHATE ADDITIVES AND THEIR USE IN OLEAGINOUS COMPOSITIONS

[75] Inventors: Jack Ryer, East Brunswick; Antonio Gutierrez, Mercerville; Harold E. Deen, Cranford, all of N.J.

[73] Assignee: Exxon Chemical Patents Inc., Linden, N.J.

[21] Appl. No.: 846,597

[22] Filed: Mar. 31, 1986

[51] Int. Cl.$^4$ .................................................. C10M 137/10
[52] U.S. Cl. ................................. 252/46.7; 252/78.5; 252/46.6; 558/80; 558/81; 558/82; 558/83; 558/86; 44/76
[58] Field of Search ....................... 558/80, 81, 82, 83, 558/86; 252/46.7, 78.5; 44/76

[56] References Cited

U.S. PATENT DOCUMENTS

| | | | |
|---|---|---|---|
| 2,280,450 | 4/1942 | Peuter et al. ........................... | 252/53 |
| 2,750,342 | 6/1956 | Mikeska et al. ....................... | 252/46.6 |
| 2,892,863 | 6/1959 | Lanham ................................. | 558/86 |
| 3,006,946 | 10/1961 | Lanham ................................. | 558/86 |
| 3,006,947 | 10/1961 | Lanham ................................. | 558/86 |
| 3,045,042 | 7/1962 | Staker ..................................... | 260/485 |
| 3,115,465 | 12/1963 | Orloff et al. ........................... | 252/49.9 |
| 3,117,091 | 1/1964 | Staker ..................................... | 252/56 |
| 3,381,022 | 4/1968 | Le Suer .................................. | 260/404.8 |
| 3,524,909 | 8/1970 | Braus et al. ............................ | 260/968 |
| 3,556,997 | 1/1971 | Leister ................................... | 252/48.6 |
| 3,576,847 | 4/1971 | Troussier et al. ...................... | 260/486 |
| 3,583,915 | 6/1971 | Myers .................................... | 252/46.6 |
| 3,652,410 | 3/1972 | Hollinghurst et al. ................ | 252/32.7 E |
| 3,655,833 | 4/1972 | Eggensperger et al. .............. | 260/948 |
| 3,773,711 | 11/1973 | Dever et al. ........................... | 558/86 |
| 3,778,375 | 12/1973 | Braid et al. ............................ | 252/49.9 |
| 3,779,928 | 12/1973 | Schlicht ................................. | 252/75 |
| 3,791,985 | 2/1974 | Eiseman, Jr. et al. ................. | 252/32.7 R |
| 3,828,084 | 8/1974 | Kaplan et al. .......................... | 260/399 |
| 3,852,205 | 12/1974 | Kablaoui et al. ...................... | 252/47.5 |
| 3,873,456 | 3/1975 | Olszewski ............................. | 558/86 |
| 3,879,306 | 4/1975 | Kablaoui et al. ...................... | 252/51.5 A |
| 3,932,290 | 1/1976 | Koch et al. ............................ | 252/49.8 |
| 4,010,106 | 3/1977 | Rothert .................................. | 252/42.7 |
| 4,010,107 | 3/1977 | Rothert .................................. | 252/42.7 |
| 4,026,812 | 5/1977 | Le Suer .................................. | 252/46.7 |
| 4,028,258 | 6/1977 | Kablaoui et al. ...................... | 252/46.7 |
| 4,029,587 | 6/1977 | Koch ..................................... | 252/48.2 |
| 4,031,017 | 6/1977 | Sabol ..................................... | 252/46.7 |
| 4,031,018 | 6/1977 | Murphy ................................. | 252/47.5 |
| 4,031,023 | 6/1977 | Musser et al. ......................... | 252/48.2 |
| 4,263,150 | 4/1981 | Clason et al. .......................... | 252/32.7 E |
| 4,344,853 | 8/1982 | Gutierrez et al. ..................... | 252/33.6 |
| 4,347,148 | 8/1982 | Davis ..................................... | 252/51.5 R |
| 4,358,509 | 11/1982 | Rysek .................................... | 428/461 |
| 4,376,054 | 3/1983 | Zinke ..................................... | 558/86 |
| 4,417,990 | 11/1983 | Clason et al. .......................... | 252/42.7 |
| 4,474,674 | 10/1984 | Gutierrez et al. ..................... | 558/81 |
| 4,511,480 | 4/1985 | Outlaw et al. ........................ | 252/8.55 E |
| 4,514,313 | 4/1985 | LeCoent ................................ | 252/42.7 |
| 4,557,845 | 12/1985 | Horodysky et al. ................... | 558/81 |

*Primary Examiner*—William R. Dixon, Jr.
*Assistant Examiner*—Ellen McAvoy
*Attorney, Agent, or Firm*—R. A. Maggio; M. B. Kapustij

[57] ABSTRACT

The present invention provides a novel cyclic phosphate such as 1,3-dioxa-2-phospha-6-thia-cyclooctane-2-(dodecylthiodi(ethyleneoxy)-2-oxide, and its use as an anti-wear, anti-oxidant, and/or friction modifying agent for oleaginous compositions such as fuels, and lubricating oils particularly automatic transmission fluids. A new use of overbased metal phenates and/or sulfonates as friction stability promoters for conventional friction modifying agents is also provided.

85 Claims, No Drawings

CYCLIC PHOSPHATE ADDITIVES AND THEIR USE IN OLEAGINOUS COMPOSITIONS

BACKGROUND OF THE INVENTION

The present invention relates to hydrocarbon soluble or dispersible cyclic phosphates, their method of preparation and their utility as an additive for oleaginous compositions including, fuel oil, lubricating oils, including greases, industrial oils, gear oils, power transmitting fluids, and engine lubricating oils.

There are many instances, as is well known, particularly under boundary lubrication conditions where two moving surfaces in contact with each other must be lubricated, or otherwise protected, so as to prevent wear, and to insure continued movement. There are other instances where friction between two rubbing surfaces is sought to be modified but not necessarily minimized. By controlling friction between two surfaces, the power required to impart movement from one surface to another is also controlled.

For example, a specialized property sought to be imparted to certain lube oil compositions adapted for use as an automatic transmission fluid is the friction modification characteristic of the fluid. This property distinguishes automatic transmission fluids (ATF) from other lubricants, and in fact between types of ATF as well. Such characteristic quality has received the most attention by both the transmission manufacturers and fluid producers for many years. This attention stems from the fact that the friction requirements of an ATF are unique and depend on the transmission and clutch design, as well as on the type of clutch plate material used.

Another property sought to be imparted to lubricating oil compositions including automatic transmission fluids is reduced wear such as bearing and power component wear.

As is also well known, both wear and friction modification can be controlled through the addition of suitable additives with varying degrees of success.

While there are many known additives which may be classified as antiwear, or friction modifying agents, it is also known that many of these additives act in a different physical or chemical manner and often compete with one another, e.g. they may compete for the surface of the moving metal parts which are subjected to lubrication. Accordingly, extreme care must be exercised in the selection of these additives to insure compatibility and effectiveness.

The metal dihydrocarbyl dithiophosphates are one of the additives which are known to exhibit antioxidant and antiwear properties. The most commonly used additives of this class are the zinc dialkyl dithiophosphates (ZDDP) which are conventionally used in lubricant compositions. While such zinc compounds afford excellent oxidation resistances and exhibit superior antiwear properties, it has heretofore been believed that the same significantly limits the ability to control the friction modification properties of the fluid.

Both anti-wear and friction modifying agents function by forming a coating on the surface of the moving metal parts. The coating bonds are generally effected physically and/or chemically. Consequently, if the bonding between the anti-wear agent and the metal part is stronger than the bonding between the friction modifying agent and the metal part, the anti-wear agent will displace the friction modifying agent at metal surface, i.e. at the metal/fluid lubrication boundary interface. This results in a loss in the ability of the friction modifying agent to exert its intended effect.

Unfortunately, while ZDDP is recognized as an industry wide standard for imparting anti-wear properties to lubricating compositions, it has been found that it also exhibits a greater affinity for the metal surface than available friction modifying agents.

Various tests have been designed by auto manufacturers for measuring ATF friction and anti-wear properties which if passed are indicative of the fact that such properties will match the requirements of particular transmission designs and result in transmission durability and smooth shifting under a variety of road conditions.

Friction modification is typically evaluated on an SAE No. 2 friction apparatus. In this test, the motor and flywheel of the friction machine (filled with fluid to be tested) are accelerated to constant speed, the motor is shut off and the flywheel speed is decreased to zero by application of the clutch. The clutch plates are then released, the flywheel is again accelerated to constant speed, and the clutch pack which is immersed in the test fluid is engaged again. This process is repeated many times with each clutch engagement being called a cycle.

During the clutch application, friction torque is recorded as a function of time. The friction data obtained are either the torque traces themselves or friction coefficients calculated from the torque traces. The shape of the torque trace desired is set by the auto manufacturers. One way of expressing this shape mathematically, is to determine the torque: (a) when the flywheel speed is midway between the maximum constant speed selected and zero speed (such torque measurement is referred to herein as $T_D$) and (b) when as the flywheel speed approaches zero rpm (such torque measurement is referred to herein as $T_O$). Such torques can then be used to determine the torque ratio which is expressed as $T_O/T_D$, in which case the typical optimum value thereof is 1, or alternatively, to determine the torque differential $T_O-T_D$; the typical optimum value of which is 0. (Thus, the optimum target value is achieved when $T_O=T_D$ provided $T_D$ is within acceptable limits.) As the $T_O/T_D$ increasingly exceeds 1, a transmission will typically exhibit shorter harsher shifts as it changes gears. On the other hand as $T_O/T_D$ decreases below 1, there is an increasingly greater danger of clutch slippage when the transmission changes gears. Similar considerations apply with respect to $T_O-T_D$ relative to the 0 target value.

Notwithstanding the above ideal target values, a $T_O/T_D$ which exceeds 1, or a $T_O-T_D$ which exceeds 0 is considered more undesirable than when $T_O/T_D$ is less than 1 or $T_O-T_D$ is less than 0. In short, harsh shifting is much more unacceptable than possible slippage.

While many automatic transmission fluids can achieve target values of $T_O/T_D$ after a minimum number of cycles, it becomes increasingly more difficult to sustain such target values as the number of cycles are increased, e.g. to 18,000 as employed in the HEFCAD test. The ability of an ATF to sustain such desired friction properties is referred to herein as friction stability. Friction instability is a particularly significant problem when the ATF contains ZDDP. It is believed that as the ATF ages under the influence of the heat of friction, the ZDDP tends to break down and the decomposition products displace conventional friction modifiers at the metal/fluid lubrication boundary interface to an even greater extent than ZDDP itself. As a result, the fluid exhibits friction instability.

Attempts to solve the problem of friction instability by simply adding more friction modifier have not met with success because this tends to reduce the breakaway static torque ($T_S$) of the fluid. This parameter when expressed as the breakaway static torque ratio ($T_S/T_D$) reflects the relative tendency of engaged parts, such as clutch packs, bands and drums, to slip. If this value is too low, the slippage can impair the driveability and safety of the vehicle.

Replacing ZDDP as an anti-wear additive to improve friction stability has also been difficult to achieve.

Very recently, more stringent requirements relating to automatic transmission fluids have been set by one or more auto manufacturers, e.g. as a result of fuel economy goals. The desire to enhance fuel economy has resulted in downsizing of cars and power trains, smaller engines and higher shift speeds, and increased usage of torque converter clutches, sprag clutches, and a shift to front wheel drive. The increased use of sprag clutches in automatic transmissions has caused a wear problem to surface which is extremely difficult to solve. Under high speed conditions, the inner race of the sprag clutch wears excessively. When this happens, there is a tendency for the sprags to flip and render the clutch inoperative.

Thus, transmission designs have undergone radical changes, thereby necessitating the formulation of ATF additives capable of meeting new and more stringent property requirements needed to match such design changes.

No base oil alone can even approach the many special properties required for ATF service. Consequently, it is necessary to employ several chemical additives, each of which is designed to impart or improve a specific property of the fluid. Consequently, it becomes particularly advantageous when one additive can perform more than one function, thereby reducing the number of additives needed to be present in the formulation.

Accordingly, there has been a continuing search for new additives possessed of one or more properties which render them suitable for use in ATF compositions, as well as other oleaginous compositions. The present invention was developed in response to this search.

U.S. Pat. No. 2,750,342 discloses hydrocarbylthio carbitol phosphates for use in improving the load carrying properties of a lubricating oil composition which phosphates exhibit a low pour point and high viscosity index. The carbitol portion of the phosphate is typically derived by reacting alkylene oxides with alcohols or mercaptans.

U.S. Pat. No. 3,828,084 discloses noncyclic thio phosphate esters for use as surface active agents. The thio phosphates are prepared by reacting an organic material with a phosphorous sulfide, e.g. $P_2S_5$. The organic material may be any non-ionic surface active condensation product of from 1 to 150 moles of a $C_2$ to $C_4$ alkylene oxide with a suitable organic compound having about 5 to about 40 or more carbon atoms. Representative organic materials which are reacted with the phosphorous sulfide as disclosed at Column 7 include dodecyl mercaptan reacted with 6 moles of ethylene oxide. The resulting product can be characterized as an alkylthio carbitol phosphate. The thio phosphates disclosed in this patent may be used as petroleum additives. More specifically, they can be used as detergents or dispersants, in gasoline or in other fuels and they are useful in motor oils for detergency, sludge suspension, metal deactivation, etc.

U.S. Pat. No. 4,511,480 discloses phosphate esters of oxyalkylated thiols for use as corrosion inhibitors for ferrous metals in deep gas wells.

U.S. Pat. No. 4,263,150 discloses the use of metal salts, e.g. zinc salts, of phosphoro dithioic acids in combination with tri-organo phosphites to reduce the corrosive effect of the metal salt on copper. Suitable organic radicals of the tri-organo phosphites include substituted hydrocarbon radicals such as alkoxy, and alkyl sulfoxy.

U.S. Pat. No. 3,791,985 discloses sulfur containing phosphate esters of thio esters of phenols and alkoxylated phenols for use as additives to lubricants, such as mineral oils, especially cutting oils, and other working applications, gear lubricants, etc.

U.S. Pat. No. 2,280,450 describes hydrocarbon oils of improved resistance to corrosion containing a small amount of a substantially stable oil-soluble water-insoluble reaction product of tricresyl phosphite and octyl phenoxyethanol. The mole ratio of tricresyl phosphite to octyl phenoxyethanol varies from 1:1 to about 1:2.5. The reaction product is described as a complex ester of phosphorous acid, which may or may not contain unreacted octyl phenoxyethanol.

U.S. Pat. No. 3,583,915 provides industrial fluid compositions and lubricant compositions containing improved load-carrying additives, including a diorgano hydrogen phosphonate in which at least one organic group in an aliphatic group containing at least 14 carbon atoms in admixture with an active sulfur compound.

U.S. Pat. No. 3,652,410 provides multifunctional lubricant additive compositions and lubricating oils containing, among other things, an organic acid phosphate or organic phosphite containing at least one alkyl or alkenyl group having from about 12 to about 24 carbon atoms. Also present is a mineral oil soluble or dispersible basic detergent, a mineral oil anti-oxidant, a sulfurized fat, or an alkyl sulfide or alkyl polysulfide.

U.S. Pat. Nos. 4,346,148 and 4,358,509 describe reaction products of alkoxylated alkyl phenol and a phosphorus trihalide which are included in lubricating compositions useful in metal-working operations, imparting corrosion resistance, extreme pressure properties, and protection against wear of working parts.

U.S. Pat. No. 3,115,465 provides antioxidant combinations for organic materials, including lubricants, comprising an oil-soluble alkyl, alkoxyalkyl, haloalkyl, cycloalkyl, halocycloalkyl, aralkyl, aryl, alkaryl, haloaryl or haloalkaryl phosphite ester; and from about 0.01 to about 5, preferably 0.25 to 2%, by weight, based on the oil, of a methylene bis-phenol.

Co-assigned U.S. patent application Ser. No. 612,666 filed May 21, 1984, discloses alkoxypolyethyleneoxy phosphite esters for use as water tolerance improving additives for lubricating oil compositions.

U.S. Pat. No. 3,524,909 discloses hydrocarbyl thioalkylene phosphites as thermal stabilizers for polyolefins. The alkylene group of the phosphite contains from 2 to about 20 carbon atoms and may be straight chain or branched. Additional inert substituents can be present, such as hydroxyl, nitro, alkoxy, halogen, and cycloaliphatic and aromatic groups. Thus, while the alkylene group may contain an alkoxy substituent, the alkylene group is not disclosed to contain repeating alkylene oxide groups. The nature of the polyolefins which are thermally stabilized by the subject phosphites is not disclosed in this patent.

U.S. Pat. No. 3,655,833 discloses hydroxybenzyl thioalkylene phosphites for use as a thermal stabilizer of organic polymer compounds against decomposition by heat, oxygen, and/or light. The alkylene group of the thio phosphite may also be replaced with a carboxy substituted alkylene group. Thus, the phosphites disclosed in this patent do not contain repeating alkylene oxide groups.

U.S. Pat. Nos. 3,045,042 and 3,117,091 both disclose partial esters of alkenyl succinic anhydride with a variety of polyhydric alcohols such as 2,2'-thiodiethanol as rust preventive additives in petroleum fractions such as gasoline and other fuels. U.S. Pat. Nos. 3,576,847 and 3,556,997 disclose sulfinyl-containing alkenyl succinates useful as dispersants, corrosion inhibitors and anti-wear agents in lubricating oil and fuel compositions, U.S. Pat. No. 3,381,022 generally discloses esters of $C_{50}$ and higher hydrocarbon succinic acids suitable as additives in oils and fuels as well as being suitable plasticizers, detergents and emulsifiers.

U.S. patent application Ser. No. 359,801, filed Mar. 19, 1982, discloses and claims power transmitting fluid compositions containing the free esters of alkenyl succinic anhydride and polyhydric alcohols such as 2,2'-thiodiethanol.

U.S. patent application Ser. No. 763,254, filed Aug. 7, 1985, discloses certain metal salt (e.g. Ca), succinate esters and their use as friction modifiers.

U.S. Pat. No. 4,344,853 discloses zinc and nickel salts of the succinate esters, of thio-bisalkanols as anti-oxidants.

U.S. patent application Ser. No. 672,420, filed Nov. 16, 1984, discloses a two-component friction modifying combination of (a) the succinate ester of thio-bisalkanols and succinic anhydride and (b) an alkyl or alkenyl diphosphite ester such as oleyl phosphite.

SUMMARY OF THE INVENTION

The present invention is based in part on the discovery that certain cyclic phosphates possess multifunctional properties including those of anti-wear, friction modification, and anti-oxidation. In addition, such phosphates are stable and hence do not severely, adversely affect friction stability of automatic transmission fluids, nor do such phosphates exhibit copper corrosion to the extent of ZDDP. In short, such cyclic phosphates are considered a substitute for ZDDP in uses conventionally applied to ZDDP but with many more advantages associated therewith.

The cyclic portion of the phosphate contains at least three hetero atoms including phosphorus, and at least 2 carbon atoms within the ring. The cyclic portion of the phosphate is considered important to the function thereof because it is believed to contribute to thermal and frictional stability of the formulation, as well as to anti-oxidation. The organo thio portion of the phosphate is considered important to friction modification and anti-wear properties.

In a preferred embodiment of the present invention, the cyclic phosphate is employed in a 3-component combination of additives which further includes a succinate ester friction modifier and a metal sulfonate and/or metal phenate, preferably overbased, friction stability promoter. This combination of additives is particularly suited to meeting the stringent ATF requirements from the standpoint of the proper balance of anti-wear, friction modification and stability, anti-oxidation and corrosion resistance properties. This combination also enables one to eliminate any separate copper anti-corrosion additive which would otherwise have to be employed when using ZDDP.

Another aspect of the present invention is directed to the discovery that metal phenates and sulfonates act as friction modification stability promoters in conjunction with conventional friction modifiers.

Accordingly, in one aspect of the present invention there is provided an oil soluble cyclic phosphate which can be represented by the structural formula:

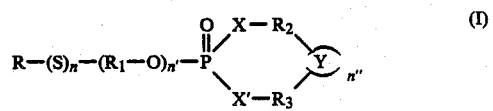

wherein R can represent alkyl, alkenyl, cycloalkyl, aralkyl, alkaryl; n is a number which can vary from 1 to about 3; $R_1$ is alkylene, n' is a number which can vary from about 1 to about 12; X and X' which may be the same or different can independently represent —O—, —NH— or —S—; $R_2$ and $R_3$ which may be the same or different can independently represent substituted or unsubstituted alkylene; n" can represent the number 0 or 1; and Y can represent —O—, —NH—, —S—, —S—S— or —CH$_2$— when n" is 1; said $R_2$ and $R_3$ being joined together and constituting part of a cyclic hetero ring structure when n" is 0.

In another aspect of the present invention, there is provided an oleaginous composition comprising an oleaginous material selected from the group consisting of fuels and lubricating oil and said above-described cyclic phosphate.

In a further embodiment of the present invention, there is provided an oil soluble reaction product of an organo phosphorus oxy dichloride and a cyclizing agent, which reactive components are described in the specification.

In a still further embodiment of the present invention, there is provided a lubricating oil composition adaptable for use as an automatic transmission fluid comprising said cyclic phosphate.

In another embodiment of the present invention, there is provided a lubricating oil composition adaptable for use as a power transmitting fluid which comprises a lubricating oil having dissolved therein at least one of the aforedescribed cyclic phosphates, at least one succinate ester friction modifier or metal salt thereof, and at least one metal phenate, sulfurized metal phenate, or metal sulfonate friction stability improver, which succinate ester and metal phenate or sulfurized metal phenate are hereinafter described.

In still another embodiment of the present invention there is provided a process for improving the frictional stability properties of a lubricating oil composition which when adapted for use as a power transmitting fluid contains a friction modifier which comprises adding to said lubricating oil composition at least one overbased: metal phenate, sulfurized metal phenate, or metal sulfonate.

DESCRIPTION OF PREFERRED EMBODIMENTS

The cyclic phosphate additives of the present invention can be represented by the structural formula:

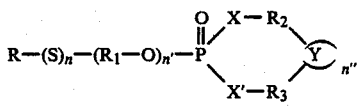

(I)

wherein R represents alkyl (preferably straight chain alkyl), typically about $C_6$ to about $C_{30}$, preferably about $C_{10}$ to about $C_{20}$, and most preferably about $C_{12}$ to about $C_{18}$ alkyl, alkenyl (preferably straight chain alkenyl), typically about $C_6$ to about $C_{30}$, preferably about $C_{10}$ to about $C_{20}$, and most preferably about $C_{12}$ to about $C_{18}$ alkenyl, cycloalkyl, typically about $C_5$ to about $C_{10}$, preferably about $C_6$ to about $C_8$, and most preferably about $C_6$ cycloalkyl, aralkyl and alkaryl wherein the aryl portion thereof contains from 6 to 10, preferably 6, carbons and the alkyl portion thereof contains typically about 2 to about 20, preferably, 5 to 10 carbons; n is a number which can vary from 1 to about 3, preferably 1; $R_1$ is alkylene (preferably straight chain alkylene) typically about $C_1$ to about $C_4$ (e.g. $C_2$ to $C_4$), preferably about $C_1$ to $C_3$ (e.g. $C_2$ to $C_3$), most preferably about $C_1$ to $C_2$ (e.g. $C_2$) alkylene; n' is a number which can vary from about 1 to about 12 (e.g. 2 to 12), preferably from about 1 to about 9 (e.g. 2 to 6), and most preferably from about 1 to about 6 (e.g. 2 to 4); X and X' which may be the same or different independently can represent —O—, —NH— or —S—; $R_2$ and $R_3$ which may be the same or different can independently represent substituted (preferably mono- or disubstituted), or most preferably, unsubstituted, alkylene (preferably straight chain alkylene), typically about $C_1$ to about $C_3$, preferably about $C_1$ to about $C_2$ alkylene, said substitutents being selected from at least one member of the group consisting of (a) alkyl, typically $C_1$ to about $C_6$, preferably $C_1$ to about $C_4$ alkyl; (b) cycloalkyl, typically $C_4$ to about $C_8$, preferably $C_4$ to about $C_6$ cycloalkyl; (c) aryl, typically $C_6$ to $C_{10}$, preferably $C_6$ aryl; (d) aralkyl or alkaryl, typically aralkyl or alkaryl wherein the alkyl portion thereof contains up to 6 carbons and the aryl portion thereof contains 6 carbons; (e) alkyl (e.g. methyl) thio alkyl, alkyl (e.g. methyl) thio alkaryl, alkyl (e.g. methyl) thio aralkyl, alkyl (e.g. methyl) thio cycloalkyl, wherein the alkyl, alkaryl, aralkyl and cycloalkyl portions thereof can be as described immediately above in connection with the description of $R_2$ and $R_3$, and (f) hydroxy (preferably terminal hydroxy) alkyl, preferably $C_1$ to $C_4$ hydroxy alkyl; n'' represents the number 1 or 0; Y can represent —O—, —NH—, —S—, —S—S or —CH$_2$— when n'' is 1, and $R_2$ and $R_3$ are joined and together constitute part of a cyclic hetero ring structure when n'' is 0.

The hydrocarbyl group constituting R of Formula I may be branched or cyclic but preferably is straight chain. When R constitutes cycloalkyl, it may be substituted with a $C_1$ to $C_{10}$, preferably $C_3$ to $C_{10}$ alkyl, preferably straight chain alkyl, group. Since it is desired to impart a cyclic structure to the phosphate, it will be recognized that the nature of the identity of $R_2$ and $R_3$ group of Formula I will be controlled, in part, by stearic considerations which are conducive to ring formation.

Representative examples of suitable R groups of Formula (I) include hexyl, heptyl, octyl, 2-ethylhexyl, isooctyl, tertiary-octyl, nonyl, isononyl, tertiary-nonyl, secondary-nonyl, decyl, isodecyl, undecyl, dodecyl, tridecyl, palmityl, stearyl, isostearyl, octenyl, nonenyl, decenyl, dodecenyl, oleyl, linoleyl and linolenyl, cyclooctyl, benzyl, octylphenyl, dodecylphenyl, and phenyloctyl.

The preferred R group is n-dodecyl.

The non-cyclic portion of the organo phosphate of Formula I is typically derived from a hydrocarbyl thioether alcohol or mixture thereof.

The hydrocarbyl thioether alcohols can be prepared by conventional methods by reacting a mercaptan and appropriate alkylene oxide, such as ethylene oxide, propylene oxide and butylene oxide, in accordance with the following equation:

(Eq. 1)

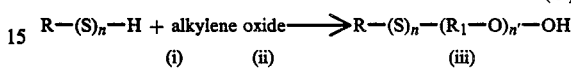

(i)   (ii)   (iii)

wherein R, $R_1$ and n' are as described in Formula (I). The value of n' in Equation 1 will vary depending on the molar ratio of alkylene oxide to thiol. Preferably the oxyalkylation reaction is conducted to achieve an n' value of two or greater since this increases the friction modification properties of the final cyclic phosphate. Alternatively, a terminal olefin can be reacted with a compound of the formula HS-($R_1$-O)$_{n'}$-H to form the same product of Equation 1.

Accordingly, while any mole ratio of alkylene oxide to thiol effective to achieve the recited n' values of Formula I may be employed, it is contemplated that such effective mole ratios will vary typically from about 1:12 to abut 1:2, preferably from about 1:6 to about 1:3, and most preferably from about 1:5 to about 1:3.

The hydrocarbyl thioether alcohols are in turn used to prepare organo phosphorous oxy dichloride intermediates, which intermediates are further reacted with various reagents to replace the dichloride with the cyclic ring structure illustrated in Formula I.

The organo phosphorous dichlorides can conveniently be synthesized by reacting the hydrocarbyl thioether alcohols with phosphorus oxytrichloride in a suitable solvent such as tetrahydrofuran at about 5° to 10° C. The phosphorus trichlorides and ether alcohols are typically reacted at a 1:1 molar ratio preferably in the presence of a base, such as triethylamine to scavenge hydrogen chloride produced in the reaction. The general reaction sequence can be illustrated as follows:

(Eq. 2)

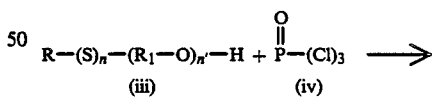

(iii)   (iv)

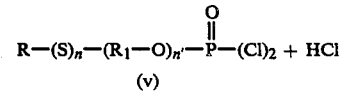

(v)

wherein R, $R_1$, n, and n' are as described in connection with Formula I.

Representative examples of suitable hydrocarbyl thio alkyleneoxy phosphorusoxy dichloride intermediates which can be employed include those wherein the organo portion is selected from octyl thio di(ethyleneoxy); dodecyl thio di(ethyleneoxy); isooctyl thio tri(ethyleneoxy); 2-ethylhexyl thio tetra(ethyleneoxy); nonyl thio di(ethyleneoxy); isodecyl thio tri(ethyleneoxy); palmityl thio tetra(ethyleneoxy); stearyl thio tri(ethyleneoxy); stearyl thio di(ethyleneoxy); octyl thio tri(ethyleneoxy); nonyl thio tetra(ethyleneoxy); octadecyl thio (ethyleneoxy); octadecyl thio di(ethyleneoxy); octyl dithio di(ethyleneoxy); dodecyl dithio di(propyleneoxy); dodecyl thio tri(butyleneoxy); tetradecyl thio tetra(ethyleneoxy); isooctyl thio di(butyleneoxy); 2-ethylhexyl thio tetra(ethyleneoxy); decyl thio di(ethyleneoxy); nonyl thio tri(ethyleneoxy); dodecyl thio di(propyleneoxyl); isodecyl thio tri(propyleneoxy); linoleyl thio(ethyleneoxy); cyclooctyl thio tri(ethyleneoxy); benzyl thio di(ethyleneoxyl); octylphenyl thio tetra(propyleneoxy); phenyldodecyl thio di(butyleneoxy); dodecyl thio (ethyleneoxy); and mixtures thereof.

The preferred organo phosphorus oxy dichloride intermediates are those wherein the organo portion is selected from n-dodecyl thio di(ethyleneoxy); and n-octadecyl thio di(ethyleneoxy).

The reagent which is reacted with the organo phosphorusoxy dichloride will depend on the nature of the cyclic structure sought to be imparted.

Representative examples of suitable cyclic structures can be illustrated as follows:

The cyclic phosphates can be prepared in accordance with the following general equation by reaction of the organo phosphorus oxy dichloride illustrated in Equation 2 with a cyclizing agent (vi) as follows:

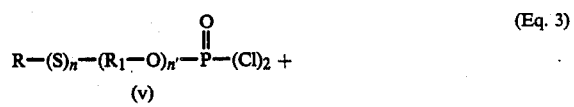

(Eq. 3)

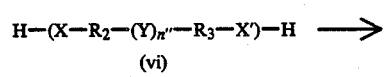

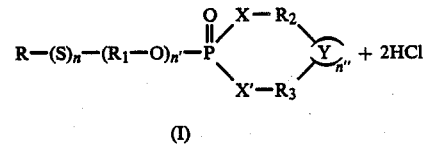

(I)

wherein R, n, $R_1$, $R_2$, $R_3$, X, X', Y and n" are as described in connection with Formula I above.

The reaction of Equation 3 is conveniently conducted

TABLE 1

| Structure No. | —X— | —X'— | —$R_2$— | —$R_3$— | n" | —Y— |
|---|---|---|---|---|---|---|
| 1 | —O— | —O— | $+CH_2+_2$ | $+CH_2+_2$ | 1 | —S— |
| 2 | —O— | —O— | $+CH_2+_2$ | $+CH_2+_2$ | 1 | —O— |
| 3 | —O— | —S— | —$CH_2$— | —$CH_2$— | 0 | N/A |
| 4 | —O— | —O— | —$CH_2$— | —$CH_2$— | 0 | N/A |
| 5 | —NH— | —NH— | —$CH_2$— | —$CH_2$— | 0 | N/A |
| 6 | —NH— | —O— | $CH_3$\\—CH—/$CH_3$ | —$CH_2$— | 0 | N/A |
| 7 | —NH— | —O— | $CH_2OH$\\—C—/$CH_2OH$ | —$CH_2$— | 0 | N/A |
| 8 | —O— | —O— | $+CH_2+_2$ | $+CH_2+$ | 1 | —O— |
| 9 | —O— | —O— | $+CH_2+_2$ | $+CH_2+_2$ | 1 | —S—S— |
| 10 | —O— | —NH— | $+CH_2+_2$ | $+CH_2+_2$ | 1 | —S—S— |
| 11 | —O— | —O— | —$CH_2$—C($CH_3$)($CH_3$)— | —$CH_2$— | 0 | N/A |
| 12 | —O— | —O— | $+CH_2+_2$ | —$CH_2$— | 0 | N/A |
| 13 | —O— | —S— | $+CH_2+_2$ | —$CH_2$— | 0 | N/A |
| 14 | —S— | —S— | $+CH_2+_2$ | $+CH_2+_2$ | 0 | N/A |
| 15 | —O— | —NH— | $+CH_2+_2$ | $+CH_2+_2$ | 1 | —S— |
| 16 | —O— | —NH— | $+CH_2+_2$ | $+CH_2+_2$ | 1 | —NH— |
| 17 | —S— | —S— | $+CH_2+_2$ | $+CH_2+_2$ | 1 | —S— |
| 18 | —O— | —O— | —$CH_2$— | —$CH_2$— | 1 | S |
| 19 | —O— | —O— | $+CH_2+_3$ | $+CH_2+_3$ | 1 | S |
| 20 | —O— | —O— | $+CH_2+_3$ | —$CH_2$— | 1 | S |
| 21 | —O— | —O— | —$CH_2$—CH($CH_3$)— | —$CH_2$— | 0 | N/A |

N/A = Not Applicable

The preferred cyclic structures contain 5 to 8 members in the ring.

The most preferred cyclic phosphates include 1,3,6-trioxa-2-phospha-cyclooctane-2-(dodecylthiodi(ethyleneoxy))-2-oxide and 1,3-dioxa-2-phospha-6-thia-cyclooctane-2-(dodecylthiodi(ethyleneoxy))-2-oxide.

in a suitable solvent such as tetrahydrofuran, at about a 1:1 molar ratio of the organophosphorus oxy chloride and cyclizing agent of Formula (vi). The reaction typically is conducted at a temperature of about 0 to about 30, preferably about 10° to about 20° C. under atmospheric pressure. Since as can be seen from Equation 3, 2 moles of HCl are liberated in the reaction, a basic substance such as triethylamine (e.g. 1 mole/mole HCl liberated) is employed to absorb the same in appropriate stoichiometric amounts.

The triethylamine hydrochloride salt precipitates as a white salt. The reaction mixture is filtered and the cyclic phosphate is recovered from the filtrate.

While the structure represented by Formula (I) is believed to depict the primary active component produced in accordance with Equation 3, it is recognized and contemplated that the final product therein can comprise a mixture of phosphates containing minor amounts (e.g. less than 20, preferably less than 10, most preferably less than 5 mole %) of phosphate by-products which do not necessarily correspond to the Formula I structure.

Furthermore, it will be recognized that alternatively a cyclic phosphorus oxy chloride can be synthesized first and subsequently reacted with a hydrocarbyl thio ether alcohol to form the cyclic phosphate of Formula (I).

The cyclic phosphates of the present invention have been found to possess multifunctional properties including anti-wear, friction-modification, friction stability, anti-oxidant, and copper corrosion resistance properties.

Accordingly, the cyclic phosphates are used by incorporation and dissolution into an oleaginous material such as fuels and lubricating oils.

When the cyclic phosphates of this invention are used in normally liquid petroleum fuels such as middle distillates boiling from about 150° to 800° F., including kerosene, diesel fuels, home heating fuel oil, jet fuels, etc., a concentration of the additive in the fuel in the range of typically from about 8 to about 400, preferably 15 to about 200, and most preferably 20 to about 100 ppm, parts by weight of the total composition, will usually be employed. The cyclic phosphates can be employed in fuels as anti-oxidants to stabilize the same against premature oxidation.

The cyclic phosphates find their primary utility in lubricating oil compositions which employ a base oil in which the additives are dissolved or dispersed.

Such base oils may be natural or synthetic although the natural base oils will derive a greater benefit.

Thus, base oils suitable for use in preparing lubricating compositions of the present invention include those conventionally employed as crankcase lubricating oils for spark-ignited and compression-ignited internal combustion engines, such as automobile and truck engines, marine and railroad diesel engines, and the like. Particularly advantageous results are achieved by employing the cyclic phosphate additives of the present invention in base oils conventionally employed in power transmitting fluids such as automatic transmission fluids, tractor fluids, universal tractor fluids and hydraulic fluids, heavy duty hydraulic fluids, power steering fluids and the like. Gear lubricants, industrial oils, pump oils and other lubricating oil compositions can also benefit from the incorporation therein of the additives of the present invention.

Thus, the additives of the present invention may be suitably incorporated into synthetic base oils such as alkyl esters of dicarboxylic acids, polyglycols and alcohols; polyalphaolefins, alkyl benzenes, organic esters of phosphoric acids, polysilicone oil, etc.

Natural base oils include mineral lubricating oils which may vary widely as to their crude source, e.g. whether paraffinic, naphthenic, mixed, paraffinic-naphthenic, and the like; as well as to their formation, e.g. distillation range, straight run or cracked, hydrofined, solvent extracted and the like.

More specifically, the natural lubricating oil base stocks which can be used in the compositions of this invention may be straight mineral lubricating oil or distillates derived from paraffinic, naphthenic, asphaltic, or mixed base crudes, or, if desired, various blended oils may be employed as well as residuals, particularly those from which asphaltic constituents have been removed. The oils may be refined by conventional methods using acid, alkali, and/or clay or other agents such as aluminum chloride, or they may be extracted oils produced, for example, by solvent extraction with solvents of the type of phenol, sulfur dioxide furfural, dichlorodiethyl ether, nitrobenzene, crotonaldehyde, molecular sieves, etc.

The lubricating oil base stock conveniently has a viscosity of typically about 2.5 to about 12, and preferably about 2.5 to about 9 cst. at 100° C.

The lubricating oil base stock typically is adapted to perform a selected function by the incorporation of additives therein to form lubricating oil compositions.

As indicated above, one broad class of lubricating oil compositions suitable for use in conjunction with the cyclic phosphate additives of the present invention are power transmitting fluids, including automatic transmission fluids, hydraulic fluids, heavy duty hydraulic fluids, power steering fluids, tractor fluids, tractor universal oils, and the like.

The benefits of the additives of the present invention are particularly significant when employed in a lubricating oil adapted for use as an automatic transmission fluid.

Power transmitting fluids, such as automatic transmission fluids, as well as lubricating oils in general, are typically compounded from a number of additives each useful for improving chemical and/or physical properties of the same. The additives are usually sold as a concentrate package in which mineral oil or some other base oil is present. The mineral lubricating oil in automatic transmission fluids typically is refined hydrocarbon oil or a mixture of refined hydrocarbon oils selected according to the viscosity requirements of the particular fluid, but typically would have a viscosity range of 2.5–9, e.g. 3.5–9 cst. at 100° C. Suitable base oils include a wide variety of light hydrocarbon mineral oils, such as, naphthenic base, paraffin base, and mixtures thereof.

Representative additives typically present in such packages as well as in the final formulation include viscosity index (V.I) improvers, corrosion inhibitors, oxidation inhibitors, friction modifiers, dispersants, anti-foaming agents, anti-wear agents, pour point depressants and seal swellants.

V.I. improvers are generally high molecular weight hydrocarbon polymers or more preferably polyesters. The V.I. improvers may also be derivatized to include other properties or functions, such as the addition of dispersancy properties.

These oil soluble V.I. polymers will generally have number average molecular weights of from $10^3$ to $10^6$, preferably $10^4$ to $10^6$, e.g. 20,000 to 250,000, as determined by gel permeation chromatography or membrane osmometry.

Examples of suitable hydrocarbon polymers include homopolymers and copolymers of two or more monomers of $C_2$ to $C_{30}$, e.g. $C_2$ to $C_8$ olefins, including both alpha olefins and internal olefins, which may be straight or branched, aliphatic, aromatic, alkylaromatic, cycloaliphatic, etc. Frequently they will be of ethylene with $C_3$ to $C_{30}$ olefins, particularly preferred being the copolymers of ethylene and propylene. Other polymers can be used such as polyisobutylenes, homopolymers and copolymers of $C_6$ and higher alpha olefins, atactic polypropylene, hydrogenated polymers and copolymers and terpolymers of styrene, e.g. with isoprene and/or butadiene. The polymer may be degraded in molecular weight, for example by mastication, extrusion, oxidation or thermal degradation, and it may be oxidized and contain oxygen. Also included are derivatized polymers such as post-grafted interpolymers of ethylene-propylene with an active monomer such as maleic anhydride which may be further reacted with an alcohol, or amine, e.g. an alkylene polyamine or hydroxy amine, e.g. see U.S. Pat. Nos. 4,089,794; 4,160,739; 4,137,185; or copolymers of ethylene and propylene reacted or grafted with nitrogen compounds such as shown in U.S. Pat. Nos. 4,068,056; 4,068,058; 4,146,489 and 4,149,984.

Suitable hydrocarbon polymers are ethylene copolymers containing from 15 to 90 wt. % ethylene, preferably 30 to 80 wt. % of ethylene and 10 to 85wt. %, preferably 20 to 70 wt. % of one or more $C_3$ to $C_{28}$, preferably $C_3$ to $C_{18}$, more preferably $C_3$ to $C_8$, alpha-olefins. While not essential, such copolymers preferably have a degree of crstallinity of less than 25 wt. %, as determined by X-ray and differential scanning calorimetry. Copolymers of ethylene and propylene are most preferred. Other alpha-olefins suitable in place of propylene to form the copolymer, or to be used in combination with ethylene and propylene, to form a terpolymer, tetrapolymer, etc., include 1-butene, 1-pentene, 1-hexene, 1-heptene, 1-octene, 1-nonene, 1-decene, etc.; also branched chain alpha-olefins, such as 4-methyl-1-pentene, 4-methyl-1-hexene, 5-methylpentene-1, 4,4-dimethyl-1-pentene, and 6-methylheptene-1, etc., and mixtures thereof.

Terpolymers, tetrapolymers, etc., of ethylene, said $C_{3-28}$ alpha-olefin, and a non-conjugated diolefin or mixtures of such diolefins may also be used. The amount of the non-conjugated diolefin generally ranges from about 0.5 to 20 mole percent, preferably from about 1 to about 7 mole percent, based on the total amount of ethylene and alpha-olefin persent.

The preferred V.I. improvers are polyesters, most preferably polyesters of ethylenically unsaturated $C_3$ to $C_8$ mono- and dicarboxylic acids such as methacrylic and acrylic acids, maleic acid, maleic anhydride, fumaric acid, etc.

Examples of unsaturated esters that may be used include those of aliphatic saturated mono alcohols of at least 1 carbon atom and preferably of from 12 to 20 carbon atoms, such as decyl acrylate, lauryl acrylate, stearyl acrylate, eicosanyl acrylate, docosanyl acrylate, decyl methacrylate, diamyl fumarate, lauryl methacrylate, cetyl methacrylate, stearyl methacrylate, and the like and mixtures thereof.

Other esters include the vinyl alcohol esters of $C_2$ to $C_{22}$ fatty or mono carboxylic acids, preferably saturated such as vinyl acetate, vinyl laurate, vinyl palmitate, vinyl stearate, vinyl oleate, and the like and mixtures thereof. Copolymers of vinyl alcohol esters with unsaturated acid esters such as the copolymer of vinyl acetate with dialkyl fumarates, can also be used.

The esters may be copolymerized with still other unsaturated monomers such as olefins, e.g. 0.2 to 5 moles of $C_2$–$C_{20}$ aliphatic or aromatic olefin per mole of unsaturated ester, or per mole of unsaturated acid or anhydride followed by esterification. For example, copolymers of styrene with maleic anhydride esterfied with alcohols and amines are known, e.g. see U.S. Pat. No. 3,702,300.

Such ester polymers may be grafted with, or the ester copolymerized with, polymerizable unsaturated nitrogen-containing monomers to impart dispersancy to the V.I. improvers. Examples of suitable unsaturated nitrogen-containing monomers include those containing 4 to 20 carbon atoms such as amino substituted olefins as p-(beta-diethylaminoethyl)styrene; basic nitrogen-containing heterocycles carrying a polymerizable ethylenically unsaturated substituent, e.g. the vinyl pyridines and the vinyl alkyl pyridines such as 2-vinyl-5-ethyl pyridine, 2-methyl-5-vinyl pyridine, 2-vinyl-pyridine, 3-vinyl-pyridine, 4-vinyl-pyridine, 3-methyl-5-vinyl-pyridine, 4-methyl-2-vinyl-pyridine, 4-ethyl-2-vinyl-pyridine and 2-butyl-5-vinyl-pyridine and the like.

N-vinyl lactams are also suitable, e.g. N-vinyl pyrrolidones or N-vinyl piperidones.

The vinyl pyrrolidones are preferred and are exemplified by N-vinyl pyrrolidone, N-(1-methylvinyl) pyrrolidone, N-vinyl-5-methyl pyrrolidone, N-vinyl-3,3-dimethylpyrrolidone, N-vinyl-5-ethyl pyrrolidone, etc.

Corrosion inhibitors, also known as anti-corrosive agents, reduce the degradation of the non-ferrous metallic parts in contact with the fluid. Illustrative of corrosion inhibitors are phosphosulfurized hydrocarbons and the products obtained by reaction of a phosphosulfurized hydrocarbon with an alkaline earth metal oxide or hydroxide, preferably in the presence of an alkylated phenol or of an alkylphenol thioester, and also preferably in the presence of carbon dioxide. Phosphosulfurized hydrocarbons are prepared by reacting a suitable hydrocarbon such as a terpene, a heavy petroleum fraction of a $C_2$ to $C_6$ olefin polymer such as polyisobutylene, with from 5 to 30 weight percent of a sulfide of phosphorous for ½ to 15 hours, at a temperature in the range of 150° to 600° F. Neutralization of the phosphosulfurized hydrocarbon may be effected in the manner taught in U.S. Pat. No. 2,969,324.

Oxidation inhibitors reduce the tendency of mineral oils to deteriorate in service which deterioration is evidenced by the products of oxidation such as sludge and varnish-like deposits on the metal surfaces. Such oxidation inhibitors include alkaline earth metal salts of alkylphenolthioesters having preferably $C_5$ to $C_{12}$ alkyl side chains, e.g. calcium nonylphenol sulfide, barium t-octylphenyl sulfide, dioctylphenylamine, phenylalphanaphthylamine, phosphosulfurized or sulfurized hydrocarbons, etc.

Friction modifiers serve to impart the proper friction characteristics to an ATF as determined by the automotive industry.

Representative examples of suitable friction modifiers are found in U.S. Pat. No. 3,933,659 which discloses fatty acid esters and amides; U.S. Pat. No. 4,176,074 which describes molybdenum complexes of polyisobutenyl succinic anhydride-amino alkanols; U.S. Pat. No. 4,105,571 which discloses glycerol esters of dimerized fatty acids; U.S. Pat. No. 3,779,928 which discloses alkane phosphonic acid salts; U.S. Pat. No. 3,778,375 which discloses reaction products of a phosphonate with an oleamide; U.S. Pat. No. 3,852,205 which discloses S-carboxyalkylene hydrocarbyl succinimide, S-carboxyalkylene hydrocarbyl succinamic acid and mixtures thereof; U.S. Pat. No. 3,879,306 which discloses N-(hydroxyalkyl)alkenyl-succinamic acids or succinimides; U.S. Pat. No. 3,932,290 which discloses reaction products of di-(lower alkyl) phosphites and epoxides; and U.S. Pat. No. 4,028,258 which discloses the alkylene oxide adduct of phosphosulfurized N-(hydroxyalkyl) alkenyl succinimides; all for use as friction modifiers in automatic transmission fluids. The disclosures of which are herein incorporated by reference. The most preferred friction modifier is a class of succinate esters or metal salts thereof.

More specifically, such succinate esters are typically formed by the reaction of (1) an alkanol and (2) a hydrocarbon-substituted succinic acid or anhydride or mixtures thereof.

The alkanol can be represented by the structural formula:

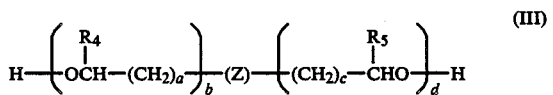

(III)

wherein $R_4$ and $R_5$ each independently can represent hydrogen, alkyl (preferably straight chain alkyl), typically $C_1$ to about $C_6$ alkyl, preferably $C_1$ to about $C_3$ alkyl, and most preferably $C_1$ to about $C_2$ alkyl; (a), (b), (c), and (d) each independently represent numbers which can vary from 1 to about 3; and Z is a linking group which is selected from —S—; —S—S—; —O—; and >$NR_6$ wherein $R_6$ can represent hydrogen, a $C_1$ to about $C_4$ alkyl group, preferably $C_1$ to about $C_3$ alkyl group, or a $C_1$ to about $C_4$ monohydroxy substituted alkyl group, preferably a terminal monohydroxy substituted alkyl group. Preferably, $R_4$ and $R_5$ are the same, the numbers represented by (b) and (d) are the same as are the numbers represented by (a) and (c), thereby resulting in a bis-alkanol.

When Z is —O—, Formula (III) can represent ethylene glycol and derivatives thereof; when Z is >$NR_6$, and $R_6$ is hydroxy substituted or hydrogen, Formula (III) can represent a diethanol amine and derivatives thereof; when $R_6$ is a monohydroxy substituted alkyl, such as —(CH$_2$)$_2$—OH, Formula (III) can represent triethanolamine and derivatives thereof.

If b or d are greater than 1, then Formula (III) is meant to express alkoxylated derivatives of the alkanols, such as ethoxylated derivatives. It should be further noted than when diethanolamine or its derivatives as expressed by Formula (III) wherein $R_6$ is hydrogen are reacted with the hydrocarbyl substituted succinic acid or anhydride, the ester product mixture formed thereby can contain an ester-amide moiety, since the NH moiety of diethanolamine is available for reaction with the acid or anhydride moiety. Likewise, when $R_6$ is hydroxy substituted alkyl, the hydroxy substitutent of $R_6$ is available for reaction with the acid or anhydride and the reaction product mixture can contain tris-ester moieties.

Notwithstanding the above, while reaction of the $R_6$ substituent with the acid or anhydride is possible, it is not intentionally facilitated. Consequently, the molar amounts of acid or anhydride employed to react with the alkanol are typically selected as though the $R_6$ substituent is inert, e.g., the acid to alcohol molar ratio will remain within the range of from about 1:1 to about 2:1 as described hereinafter in connection with mono and diesters. In such instances, mixtures of ester compounds are typically achieved.

The preferred alkanols are thio-alkanols, wherein in structural Formula (III), Z is —S—, and $R_4$ and $R_5$ are independently hydrogen, ethyl or methyl.

The most preferred alkanols are thio-alkanols wherein in structural Formula (III), (a), (b), (c) and (d) are each 1 or 2, $R_4$ is hydrogen or methyl, and $R_5$ is hydrogen, methyl or ethyl.

Representative alkanols include 2,2'-thiodiethanol; 3,3'-thiodipropanol; thio-bis ethoxyethanol; thio-bis isopropoxy isopropanol; oxy-bis ethanol; oxy-bis ethoxyethanol; 2,2'-diethanol methanamine; 2,2'-diethanol ethanamine; 2,2',2"-triethanolamine; 2,2'-diethanolamine; and mixtures thereof.

The hydrocarbon substituted succinic acid or anhydride which is reacted with the alkanol can be represented by the respective structural formulas:

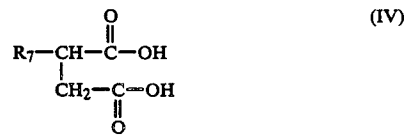

(IV)

or

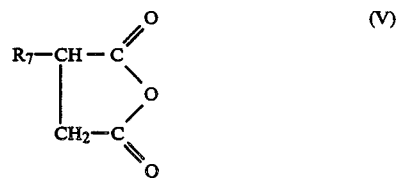

(V)

wherein $R_7$ is an aliphatic hydrocarbon group, typically a $C_{12}$ to about $C_{50}$ aliphatic hydrocarbon group (preferably a straight chain aliphatic hydrocarbon group), preferably a $C_{16}$ to about $C_{30}$ aliphatic hydrocarbon group, and most preferably a $C_{18}$ to about $C_{22}$ aliphatic hydrocarbon group. The aliphatic hydrocarbon group can be alkyl, preferably straight chain alkyl, alkenyl, preferably straight chain alkenyl, isoalkyl, or isoalkenyl.

Oligomers containing the aforedescribed number of carbon atoms are also suitable as the aliphatic hydrocarbyl group, such as oligomers of $C_2$–$C_5$ monoolefins, such as isobutene.

The aliphatic hydrocarbyl group is preferably an unsubstituted hydrocarbon group although it may contain substituents such as chlorine, bromine, sulfur, phosphorous, nitrogen or oxygen which will not affect the utility of the final product. A preferred substituent is sulfur as exemplified by 2-octadecenylthiosuccinic anhydride.

The hydrocarbyl substituted succinic acid or anhydride compounds may be prepared by the reaction of maleic anhydride with olefins, oligomeric polyolefins, or with chlorinated derivatives thereof using techniques known in the art. Succinic acids are readily produced by hydrolysis of the corresponding anhydride. Especially preferred in preparing the ester compounds are $C_{18}$ to $C_{22}$ alkenyl succinic anhydrides, such as octadecenyl succinic anhydride.

As used herein when the Z group is in fact inert, the term "monoester" or "hemiester" refers to product made from equimolar proportions of said alkanol and a succinic acid or anhydride, that is, one free hydroxyl group remains; while the term "di-ester" refers to those products using a 2:1 molar ratio of acid to alcohol wherein each hydroxyl group of the alkanol is esterified with a hydrocarbyl-substituted or polyolefin-substituted succinic acid or anhydride. In either case, at least one terminal carboxyl group of the succinic acid moiety remains, which optionally can be neutralized to form the metal salt derivative of the ester as described herein below.

Formation of the mono- and di-esters proceeds by reacting the appropriate quantities of anhydride (or acid) and alkanol with or without an inert organic solvent diluent and heating and stirring the mixture at about 50° to 150° C. until esterification of the anhydride is complete. Equimolar quantities of each reactant wll typically provide mainly the mono- (or hemi-) ester, and reaction of 2 moles of hydrocarbon substituted succinic acid or anhydride per mole of alkanol will typically provide the di-ester material. Also, useful products encompass mixtures of such mono- and di-esters as well as mixtures of metal salt mono-esters, diesters, ester-amides, and/or tris-esters depending on the identity of the Z group when constituting $>NR_6$.

The esterification reaction time is typically controlled to be from about 10 to about 30 minutes.

Insofar as yields are concerned, the reaction of an equimolar ratio of alkanol (when Z is inert) and hydrocarbyl substituted succinic anhydride will typically provide a product containing about 80% mono-ester and about 20% di-ester. The di-ester is produced in somewhat higher yields, about 90% of the product being di-ester and about 10% mono-ester when the mole ratio of succinic anhydride to alkanol is 2:1.

In view of the above, a simplified structural formula of the resulting ester product derived from the succinic acid reactant and an alkanol wherein Z is inert, can be represented as follows:

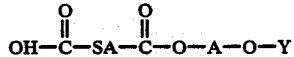 (VI)

wherein SA represents the succinic acid moiety depicted by Formula (IV) above exclusive of the terminal carboxyl groups; (A) represents the alkanol moiety depicted by Formula (III) exclusive of the terminal hydroxyl groups; Y represents hydrogen when the product is a hemi-ester, and:

 (VII)

when the product is a di-ester.

The maximum carbon chain length of the $R_7$ substituent, is affected by the propensity of increasingly longer chains to come out of solution as the fluid composition containing the same is cooled to lower and lower temperatures. The insolubilization of such substituents is undesirable because it results in agglomeration of the same as well as the formation of nucleation sites for wax crystal formation. Thus, the particular maximum substituent chain length selected will be affected by the ultimate end use for which the additive will be employed in terms of the temperature regimens to which it will be exposed.

In addition to the aforedescribed free ester as a friction modifier, the same may also be converted to the metal salt thereof, said metals being selected from the alkaline earth metals including Mg, Ca, Sr, Ba; as well as Zn, Ni, Cu, and Mo, and mixtures thereof. The preferred metals are calcium and magnesium.

The metal ester salts of the afore-described friction modifiers can be prepared by reacting the ester with a metal carboxylate, typically a $C_1$ to about $C_6$ carbon containing metal carboxylate, or a metal hydroxide. Suitable carboxylates include the acetate, propionate, and mixtures thereof. The particular metal containing reactant is typically selected to be at least partially soluble in the reaction mixture solvent containing the co-reactant ester.

Suitable solvents are typically protic and include $C_1$ to $C_5$ alkanols, such as methanol, water, or tetrahydrofuran. The preferred solvent is methanol.

The metal carboxylate or hydroxide is then typically admixed with the ester in the presence of a suitable solvent in amounts sufficient to meet the stoichiometric requirements of the reaction. More specifically, the relative proportions of the ester and metal carboxylate or hydroxide which are admixed and reacted together are determined by stoichiometric considerations which are a function of the valence of the metal of the metal carboxylate, and the mole fraction of hemi- or diester components in the ester.

Thus, when using a divalent metal in the form of a metal carboxylate and a diester, the ester and metal carboxylate are typically mixed at about a 1:1 mole ratio.

Likewise, about a 2:1 molar ratio of ester:metal carboxylate would be employed using a divalent metal and hemi-ester.

In short, typically each equivalent of free acid on the ester is admixed with about $X^{-1}$ moles of metal carboxylate or hydroxide, where X is the valence of the metal in the metal carboxylate. The metal carboxylate or hydroxide and ester are typically allowed to react completely at a temperature of from about 25° to about 80° C. until the metal ester salt precipitates from the reaction mixture. The precipitate is typically then washed with a volatile solvent and dried under a nitrogen atmosphere.

The preferred method of salt formation is described in U.S. patent application Ser. No. 750, 174, filed July, 1, 1985, the disclosure of which is herein incorporated by reference.

Dispersants maintain oil insolubles, resulting from oxidation during use, in suspension in the fluid thus preventing sludge flocculation and precipitation. Suitable dispersants include high molecular weight alkyl succinates, the reaction product of oil-soluble polyisobutylene succinic anhydride with ethylene amines such as tetraethylene pentamine and borated salts thereof.

Pour point depressants lower the temperature at which the fluid will flow or can be poured. Such depressants are well known. Typical of those additives which usefully optimize the low temperature fluidity of the fluid are $C_8$–$C_{18}$ dialkylfumarate vinyl acetate copolymers, polymethacrylates, and wax naphthalene.

Foam control is provided by an antifoamant of the polysiloxane type, e.g. silicon oil and polydimethyl siloxane.

Anti-wear agents, as their name implies, reduce wear to transmission parts. Representative of conventional anti-wear agents are zinc dialkyldithiophosphate, zinc diaryldithiophosphate and magnesium sulfonate. It is an advantage of the present invention that supplemental anti-wear agents do not have to be employed.

Some of these numerous additives can provide a multiplicity of effects, e.g. a dispersant-oxidation inhibitor. This approach is well known and need not be further elaborated herein.

Seal swellants include mineral oils of the type that provoke swelling, including aliphatic alcohols of 8 to 13 carbon atoms such as tridecyl alcohol, with a preferred seal swellant being characterized as an oil-soluble, satured, aliphatic or aromatic hydrocarbon ester of from 10 to 60 carbon atoms and 2 to 4 linkages, e.g. dihexylphthalate, as are described in U.S. Pat. No. 3,974,081.

Compositions when containing these conventional additives are typically blended into the mineral oil base in the following ranges thereby providing their normal attendant function.

| Compositions | Vol % | Wt % |
|---|---|---|
| V.I. Improver | 1–15 | 1–16 |
| Corrosion Inhibitor | 0.01–1 | .01–1.5 |
| Oxidation Inhibitor | 0.01–1 | .01–1.5 |
| Dispersant | 0.5–10 | 0.5–11 |
| Pour Point Depressant | 0.01–1 | .01–1.5 |
| Demulsifier | 0.001–0.1 | .001–0.15 |
| Anti-Foaming Agents | 0.001–0.1 | .001–0.15 |
| Anti-Wear Agents | 0.001–1 | .001–1.5 |
| Seal Swellant | 0.1–5 | 0.1–6 |
| Friction Modifiers | 0.01–1 | .01–1.5 |
| Mineral Oil Base | Balance | Balance |

In a broad sense therefore, the cyclic phosphate additives of the present invention when employed in a lubricating oil composition comprise lubricating oil, typically in a major amount, and the cyclic phosphate additive, typically in a minor amount, which is effective to impart one or more of enhanced anti-wear, anti-oxidant friction modification properties thereto, relative to the absence of the additive. Additional conventional additives selected to meet the particular requirements of a selected type of lubricating oil composition can be included as desired.

The cyclic phosphates of this invention are oil-soluble, dissolvable in oil with the aid of a suitable solvent, or are stably dispersible materials. Oil-soluble, dissolvable, or stably dispersible as that terminology is used herein does not necessarily indicate that the materials are soluble, dissolvable, miscible, or capable of being suspended in oil in all proportions. It does mean, however, that the cyclic phosphate additives, for instance, are soluble or stably dispersible in oil to an extent sufficient to exert their intended effect in the environment in which the oil is employed. Moreover, the additional incorporation of a dispersant and/or other additives may also permit incorporation of higher levels of a particular cyclic phosphate, if desired.

Representative examples of suitable oil-soluble solvents capable of assisting in the dissolution or dispersion of the cyclic phosphate in the base oil include aromatic solvents such as benzene, xylene, toluene, tetrahydrofuran, ethers such as n-propyl ether, methyl/n-amyl ether, etc.

Accordingly, while any effective amount of the cyclic phosphate additive can be incorporated into the lubricating oil composition, it is contemplated that such effective amount be sufficient to provide said lube oil composition with an amount of the additive of typically from about 0.05 to about 1.5, preferably from about 0.1 to about 1, and most preferably from about 0.3 to about 0.8%, by weight, based on the weight of said composition.

The cyclic phosphate additives of the present invention can be incorporated into the lubricating oil in any convenient way. Thus, they can be added directly to the oil by dispersing, or dissolving the same in the oil at the desired level of concentration typically with the aid of a suitable solvent such as toluene, or tetrahydrofuran. Such blending can occur at room temperature or elevated temperatures. Alternatively, the cyclic phosphate additive component may be blended with a suitable oil-soluble solvent and base oil to form a concentrate, and then blending the concentrate with lubricating oil base stock to obtain the final formulation.

When other additives are employed, it may be desirable, although not necessary, to prepare additive concentrates comprising concentrated solutions or dispersions of the cyclic phosphate together with said other additives (said concentrate additive mixture being referred to herein as an add-pack) whereby the several additives can be added simultaneously to the base oil to form the lubricating oil composition. Dissolution of the additive concentrate into the lubricating oil may be facilitated by solvents and by mixing accompanied with mild heating, but this is not essential. The concentrate or add-pack will typically be formulated to contain the cyclic phosphate and optional additional additives in proper amounts to provide the desired concentration in the final formulation when the add-pack is combined with a predetermined amount of base lubricant. Thus, the cyclic phosphate of the present invention can be added to small amounts of base oil or other compatible solvents along with other desirable additives to form concentrates containing active ingredients in amounts of typically from about 2.5 to about 90%, and preferably from about 5 to about 75%, amd most preferably from about 8 to about 50% by weight additives in the appropriate proportions.

The final formulations may employ typically about 10 wt. % of the add-pack with the remainder being oil.

When the cyclic phosphate is to be employed for its anti-wear properties in crankcase lubricating oil formulations, it is contemplated that effective amounts in the final formulations will include typically from about 0.1 to about 2, preferably 0.3 to about 1.0, and most preferably 0.4 to about 0.8% by weight of the formulation.

Other additives typically present in lubricating compositions adapted for use in crankcase oils include metal detergent, V.I. improver, dispersants including ashless dispersants, pour point depressants, other anti-wear agents and the like in conventional amounts.

All of said weight percents expressed herein are based on active ingredient (a.i.) content of the additive, and/or upon the total weight of any additive package, or formulation which will be the sum of the a.i. weight of each additive plus the weight of total oil or diluent.

It is a further embodiment of the present invention to employ a three component combination of (1) cyclic phosphate (as generally depicted by Formula I), (2) succinate ester (or metal salt thereof) as generally depicted by simplified Formula VI, and (3) at least one friction stability promoter selected from overbased: metal phenate, including sulfurized metal phenate, and/or metal sulfonate in a lubricating oil composition, e.g. power transmitting fluid, preferably adapted for use as an automatic transmission fluid.

The first two of the above 3 components have already been discribed.

Metal phenates, especially sulfurized phenates, and metal sulfonates are well known in the art to have detergent properties and are widely used as dispersants in lubricants. Such materials are used in the present invention for an entirely different purpose, namely, as a friction stability promoter.

Phenates suitable for use in accordance with the present invention include overbased alkali metal and alkaline earth metal phenates, preferably sulfurized phenates.

Non-sulfurized phenates typically are the reaction products of a phenol or substituted phenol with an alkali or alkaline earth metal base.

The substituted phenols can be mono-, di- or tri-, preferably mono-, hydrocarbyl substituted. Each hydrocarbyl substituent, which can be the same or different, can be branched, preferably straight chain, unsaturated, preferably saturated, aliphatic, aromatic, or mixed aliphatic aromatic having typically from about 1 to about 1000, preferably 10 to about 100, and most preferably from about 10 to about 50 carbon atoms. Thus, the hydrocarbyl substituent can be alkyl, alkenyl, aryl, aralkyl or alkaryl. Monoalkyl substitution is preferred. The hydrocarbyl group can comprise low molecular weight groups such as methyl, ethyl, the isomers of propyl, butyl, pentyl, hexyl, heptyl, octyl, nonyl, decyl, and the like, up to high molecular weight materials having a number average molecular weight of 10,000 or more. These hydrocarbyl substituents can be polymer olefins.

The term polymer olefins as used hereinabove refers to amorphous polymers and copolymers derived from olefinically unsaturated monomers. Such olefin monomers include olefins of the general formula $RCH=CH_2$, in which R comprises aliphatic or cycloaliphatic radical of from 1 to about 20 carbon atoms, for example, propene, isobutylene, butene-1,4-methyl-1-pentene, decene-1, vinylidene norbornene, 5-methylene-2-norbornene, etc. Other olefin monomers having a plurality of double bonds may be used, in particular diolefins containing from about 4 to about 25 carbon atoms, e.g., 1,4-butadiene, 2,3-hexadiene, 1,4-pentadiene, 2-methyl-2,5-hexadiene, 1,7-octadiene, etc. These polyolefins have number average molecular weights from about 36 to about 10,000 or higher, but preferably from about 80 to about 10,000. Of these materials, a preferred group is polypropylene or polybutylene polymers. The olefin may be a copolymer, such as an ethylene propylene copolymer or ethylene-propylene-hexadiene terpolymer, or others.

Preferred hydrocarbyl substituents have a molecular weight of about 80 to about 10,000, especially from about 80 to about 200. Many commercially available and preferred substituted phenols contain about $C_4$ to about $C_{100}$, more preferably $C_8$-$C_{20}$ substituents from polypropylene or polybutene. The hydrocarbon substituted phenol may have other substituents, such as for example, chlorine, bromine, nitro or sulfonic acid groups so long as such substitution does not interfere with the friction stability nor adversely affect the utility of the composition.

The most preferred substituent is a $C_6$ to about $C_{20}$, (e.g. $C_8$ to $C_{15}$) alkyl group.

The metal base can comprise a metal oxide, hydroxide, alcoholate, acetate and the like. The preferred metals are calcium and magnesium.

The sulfurized metal phenates are believed to contain sulfur, such as a sulfur bridge between two phenyl groups containing one, two, three, four, or more sulfur atoms. Several phenols or substituted phenols can be bridged together by a number of sulfur bridges. The sulfur can be introduced by the reaction of elemental sulfur or $SCl_2$ with phenol or substituted phenol, or by the reaction of elemental sulfur or $SCl_2$ with metal phenate or substituted phenate.

To make the corresponding overbased metal phenate or sulfurized metal phenate, the phenol or substituted phenol is typically reacted with excess metal base and the excess neutralized with an acidic gas, e.g. $CO_2$. The degree of overbasing is expressed by the Total Base Number (TBN; ASTM D664). Overbased phenates having a TBN of typically from about 30 to about 450, preferably 50 to about 350, and most preferably 70 to about 250 are suitable for use in accordance with the present invention.

Suitable oil soluble overbased metal sulfonates can be made by reacting a metal base with oil-soluble sulfonic acids. Suitable oil-soluble sulfonic acids can be aliphatic or aromatic compounds. The aromatic sulfonic acids are typically derived from benzene sulfonic acid which may be substituted with the same type and number of hydrocarbyl substituents as described above in connection with the phenates.

Thus, suitable aromatic sulfonic acids include the oil-soluble petroleum sulfonic acids, commonly referred to as "mahogany acids," aryl sulfonic acids, and alkaryl sulfonic acids. Illustrative of such sulfonic acids are dilauryl benzene sulfonic acid, lauryl cetyl benzene sulfonic acid, paraffin-substituted benzene sulfonic acids, polyolefin alkylated benzene sulfonic acids, such as polybutylene alkylated benzene sulfonic acids in which the polybutylene substituents have molecular weight of at least about 100, and preferably within the range of from about 100 to about 10,000, and polypropylene alkylated benzene sulfonic acids in which the polypropylene substituents have a molecular weight of at least about 80 and preferably within the range of from about 80 to about 10,000. Examples of other suitable sulfonic acids are diparaffin wax-substituted phenol sulfonic acids, acetyl chlorobenzene sulfonic acids, cetyl-phenol disulfide sulfonic acids, cetyl-phenol monosulfide sulfonic acids, and cetoxy capryl benzene sulfonic acids. Other suitable oil-soluble sulfonic acids are well described in the art, such as for example U.S. Pat. No. 2,616,604; U.S. Pat. No. 2,626,207; and U.S. Pat. No. 2,767,209, and others.

Non-aromatic sulfonic acids are generally made by the sulfonation of most any aliphatic hydrocarbon such as alkanes, alkenes, and the like. Also, the hydrocarbyl group may contain various substitutions which do not interfere with later reactions or end use. One preferred group of non-aromatic sulfonic acids is made by the sulfonation of polymers or copolymers, such as polymerized or copolymerized olefins as defined above in connection with phenates.

The preparation of sulfonic acids is well known. Such sulfonic acids can be prepared by reacting the material to be sulfonated with a suitable sulfonating agent, such as concentrated sulfuric acid, fuming sulfuric acid, chlorosulfonic acid or sulfur trioxide for a period of time sufficient to effect sulfonation, and thereafter separating insoluble acid sludge from the oil-soluble sulfonic acid. Overbased sulfonates are commonly made by the reaction of sulfonic acid with excess metal bases such as the oxide, hydroxide, or carbonate of alkali or alkaline earth metals. The preferred metals are Group II metals such as Mg, Ca, and Ba. The excess base is typically neutralized with an acid gas, e.g., $CO_2$. In some cases the sulfonate can be made from the metal itself or a derivative of said metal. Suitable processes for making overbased sulfonates are described in U.S. Pat. Nos. 3,126,340; 3,492,230; 3,524,814 and 3,609,076. The carbonate overbased magnesium sulfonates are preferably made from MgO and carbon dioxide in the presence of a promoter such as ethylene diamine or ammonia. However, some overbased sulfonates contain no carbonate.

Suitable overbased sulfonates have a TBN of typically about 30 to about 450, preferably 50 to about 350, and most preferably about 70 to about 250.

The preferred overbased sulfonates include calcium $C_{12}$ alkyl substituted benzene sulfonates.

Mixtures of overbased phenates and sulfonates may be employed.

Methods of making the afore-described phenates and sulfur containing phenates and sulfonates and overbasing can be found U.S. Pat. Nos. 3,966,621; 3,969,235; 3,953,519; 3,932,289; 3,923,670; 3,801,507; 3,036,971; 3,810,837; 3,761,414; 3,336,224; 3,178,368; 3,437,595; and 3,464,970.

By themselves, overbased metal phenates (including sulfurized phenates) or sulfonates exhibit essentially no friction modification properties. However, it has been found that such overbased materials especially sulfurized phenates synergistically interact with conventional friction modifiers, and particularly with the succinate ester friction modifier described above in connection with Formulas (VI) and (VII) to improve the frictional stability characteristics of an ATF (e.g. as measured by $T_O-T_D$ in the HEFCAD test), particularly when exposed to elevated temperatures for extended periods, whether ZDDP is present or not. However, the cyclic phosphates of the present invention permit elimination of ZDDP as an anti-wear agent from the ATF formulation. As discussed above, ZDDP disadvantageously affects the frictional stability of a friction modifier. Consequently, by eliminating ZDDP from the formulation in lieu of a cyclic phosphate, the metal phenate or sulfonate is permitted to impart a greater enhancement of frictional stability to the succinate ester as a result thereof.

In addition, the cyclic phosphate when employed in amounts effective to achieve desired anti-wear and anti-oxidant properties also inherently exhibits good HEFCAD friction modification properties of its own. This has the added benefit of permitting a reduction in the amount of succinate ester (and hence also the associated phenate) needed to achieve the overall desired friction modification and stability properties. It has been found that as the amount of succinate ester and/or phenate (or sulfonate) increases in an ATF, the lower the breakaway static torque becomes. As the breakaway static torque (as well as the breakaway static coefficient of friction) decreases, the bands of the automatic transmission become increasingly more susceptible to slippage. Consequently, it is extremely advantageous to be able to control, e.g. reduce, the amount of succinate ester and friction stability promoter without sacrificing the friction modifying properties of the fluid, e.g., as measured by the HEFCAD torque differential $T_O-T_D$ and stability thereof, since this permits one to simultaneously achieve both the desired breakaway static torque and HEFCAD torque differential friction characteristics.

In short, the combination of cyclic phosphate, succinate ester and friction stability promoter permit the formulator to flexibly tailor an ATF in order to achieve the balance of properties required under today's more stringent transmission manufacturers' specifications.

When a three component combination of cyclic phosphate, succinate ester and friction stability promoter is employed in a lubricating oil composition the cyclic phosphate is employed in the amounts previously described, which amounts are typically directed toward achieving acceptable anti-wear properties.

The succinate ester is employed in any amount effective to impart improved friction modification properties relative to its absence. Thus, while any effective amount of succinate ester may be employed, it is contemplated that such effective amount can vary typically from about 0.05 to about 1, preferably 0.1 to about 0.8, and most preferably 0.1 to about 0.5%, by weight, based on the weight of the final formulation containing the same.

The friction stability promoters likewise are employed in the lubricating oil formulation in an amount effective to improve the friction stability of the formulation relative to their absence. Thus, while any effective amount of friction stability promoter can be employed, it is contemplated that such effective amount will be sufficient to achieve a weight ratio of succinate ester to friction stability promoter in the final formulation of typically from about 1:1 to about 10:1, preferably 1:1 to about 8:1, and most preferably 1:1 to about 3:1.

Concentrates containing the aforedescribed components in equivalent proportions but at higher concentrations are also contemplated.

As indicated above, it has been found that the afore-described friction stability promoters have wider application for improving the friction stability characteristics of any conventional friction modifier in an ATF formulation.

Thus, the afore-described weight ratios between the succinate ester friction modifier and friction stability promoter are equally applicable to friction modifying agents in general.

The following examples are given as specific illustrations of the claimed invention. It should be understood, however, that the invention is not limited to the specific details set forth in the examples. All parts and percentages in the examples as well as in the remainder of the specification are by weight unless otherwise specified.

EXAMPLE 1

This example illustrates the preparation of the cyclic phosphate represented by the formula:

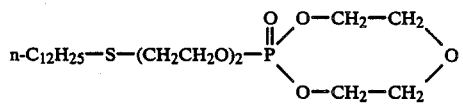

and designated herein as Phosphate A.

Thus, 290 g (1.0 mole) of n-dodecyl-thioethylene oxyethanol and 153.5 g (1.0 mole) of phosphorus oxytrichloride were dissolved in tetrahydrofuran at a temperature of about 5° to 10° C. Then, 101 g. (1.0 mole) of triethylamine were added dropwise to the reaction mixture for a period of 0.5 hr. and the contents stirred for 30 minutes. To the mixture was then added 106 g (1.0 mole) of bis(hydroxyethyl)ether followed by dropwise addition of 202 g (2.0 moles) of triethylamine while the reaction mixture was maintained between 10° to 20° C. The reaction mixture was stirred at room temperature for 3 to 4 hrs. The reaction mixture was then filtered to remove triethylamine hydrochloride as a white solid. The cyclic phosphate remains in the filtrate. The solvent was stripped and the phosphate collected as an oily residue.

EXAMPLE 2

This example illustrates the preparation of the cyclic phosphate represented by the formula:

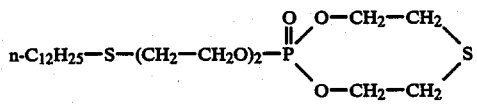

which compound is referred to herein as Phosphate B.

Thus, Example 1 was repeated using the same molar proportions of reactants with the exception that bis(hydroxyethyl)sulfide is employed instead of the bis(hydroxyethyl)ether of Example 1.

EXAMPLE 3

This example illustrates the preparation of the cyclic phosphate represented by the formula:

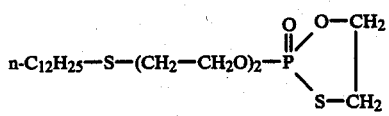

referred to herein as Phosphate C.

Thus, Example 1 was repeated using the same molar proportions of reactants as Example 1 with the exception that mercaptoethanol was employed in place of the bis(hydroxyethyl)ether of Example 1.

EXAMPLE 4

This example illustrates the preparation of the cyclic phosphate represented by the formula:

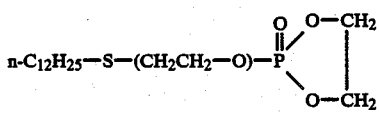

referred to herein as Phosphate D.

Thus, Example 1 was repeated using the same molar proportions of reactants as Example 1 with the exception that ethylene glycol was employed in place of the bis(hydroxyethyl)ether of Example 1.

EXAMPLE 5

This example illustrates the preparation of the cyclic phosphate having the formula:

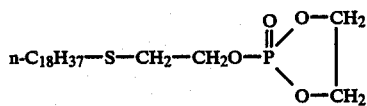

referred to herein as Phosphate E.

Thus, Example 1 was repeated using the same molar proportions of reactants with the exception that n-octadecyl thio-ethanol was used in place of the dodecyl thioethylene oxyethanol, and ethylene glycol was used in place of the bis(hydroxyethyl)ether.

EXAMPLE 6

The diester reaction product of 2-octadecenyl succinic anhydride with 2,2'-thio-bis-ethanol was prepared by adding 0.5 mole of the alcohol to a mole of the anhydride at 120° C. The reaction mixture was stirred at this temperature until the anhydride carbonyl adsorption band is absent in the IR spectrum of the reaction mixture. This compound can be represented by the formula:

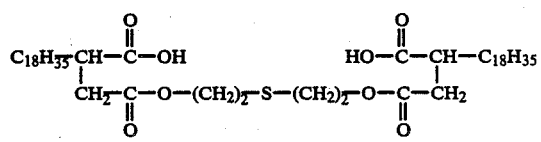

This above succinate ester friction modifier additive is designated Friction Modifier A.

EXAMPLE 7

Part A

A Base Fluid was formulated (designated herein as Base Fluid A) containing conventional amounts of a borated ashless dispersant, antioxidant, viscosity index improver, seal swellant, and Friction Modifier A (0.5 vol. %), dissolved in a paraffinic base oil.

Part B

To the Base Fluid A was added 0.43 vol. % zinc $C_4$–$C_5$ dialkyl dithiophosphate (ZDDP) and 0.3 vol. % of a copper corrosion inhibitor needed to counteract the corrosive tendencies of ZDDP. The resulting formulation is designated herein as Formulation A.

Part C

A second base fluid designated Base Fluid B was prepared which was essentially the same as Base Fluid A with the exception that it contained only 0.4 vol. % of the Friction Modifier A. To the Base Fluid B was added 0.5 vol. % of Phosphate B. The resulting formulation is designated Formulation B.

Part D

An oil formulation was prepare in accordance with Part C using Base Fluid B with the exception that 0.5 vol. % of Phosphate A of Example 1 was used in place of Phosphate B. This formulation is designated herein as Formulation C.

Part E

An oil formulation was prepared in accordance with Part D with the exception that 0.5 vol. % of Phosphate C was employed in place of Phosphate A. This formulation is designated Formulation D.

Part F

An oil formulation was prepared in accordance with Part D with the exception that 0.5 vol. % of Phosphate D was employed in place of Phosphate A. This oil formulation is designated Formulation E.

Part G

An oil formulation was prepared in accordance with Part D with the exception that 0.5 vol. % of Phosphate E was employed in place of Phosphate A. This formulation is designated Formulation F.

Part H

Formulations A to F were then tested for their antiwear properties using the FZG Gear Test.

FZG Gear Test

This test employs a gear box containing a wheel gear engaged with a pinion gear. The pinion gear is connected by an axle to a motor. The motor turns the pinion gear through the axle and the pinion gear serves to drive the wheel gear. The wheel gear is connected to a different axle which extends out of the gear box. A load is applied to the wheel gear during the test which creates resistance to the turning of the wheel gear by the pinion gear. This load is applied in several stages and increases in each stage. The load is expressed as torque (N.m) at the pinion gear.

Thus, the load of each load stage can be expressed as as follows:

| Stage No. | Torque at Pinion (N.m.) | Stage No. | Torque at Pinion (N.m.) |
|---|---|---|---|
| 1 | 3.3 | 8 | 239.3 |
| 2 | 13.7 | 9 | 302 |
| 3 | 35.3 | 10 | 372.6 |
| 4 | 60.8 | 11 | 450.1 |
| 5 | 91.1 | 12 | 534.5 |
| 6 | 135.3 | | |
| 7 | 183.4 | | |

Prior to the start of each run, the test gear box is carefully flushed twice with a suitable solvent (nonflammable). The solvent is filled above the center of the shaft axles. The machine is then turned one full rotation by hand to remove waste oil from the bearings assemblies. The complete housing is then dried thoroughly.

The test gears are likewise washed. The tooth flanks are visually inspected from a fixed viewing distance of 25 cm. Existing irregularities are noted. Test wheels with any signs of rusting or corrosion are discarded.

The pinion and wheel gears are marked in such a way that when the test pieces are reassembled, the same teeth mesh as before. After installing the pinion gear on its shaft and the wheel gear on its shaft, the test gear box is filled with the oil formulation to be tested up to the center of the shafts. A preliminary run is made at the first load stage while heating until the temperature has reached 90°±3° C. The motor and rig are turned off until the next load stage is run.

The pinion and wheel gears are disassembled at the end of each load stage, washed in solvent, allowed to cool to room temperature, washed again and this time dried with an air gun.

The test gears are then separately examined at the fixed viewing distance for changes in appearance of the flanks. Thus, smoothing of the grinding marks, scratches, scoring, siezure marks, discoloration of the tooth flanks, corrosion symptoms, deposits, the natural position, and extent of the change on the tooth flanks are all noted.

The inspected gears are then re-mounted on the shafts for the next load stage. The same oil is used and the load stages are increased until a marked deviation (e.g. increase) in deterioration of the visible appearance of the gears is observed relative to the progressive deterioration observed in previous load stages. When such deterioration is observed the oil fails that load stage and the test is completed.

The following is a summary of the test conditions of the FZG test.

| Test Conditions | |
|---|---|
| Complete Revolutions Of Wheel Gear per Load Stage | 21,700 |
| Pinion Speed | 2,170 RPM |
| Drive Gear | Pinion |
| Lubrication | Splash or Dip |
| Oil Temp. at Beginning of Test Run | 90 ± 3° C. |
| Amount of Oil Needed (Center of Shaft) | 1.25 L |
| Running Time Per Load Stage | 15 Min. |

The results of testing each formulation are summarized at Table 1, Runs 1 to 6.

TABLE 1

| Run No. | Base Fluid | Antiwear Additive | Highest FZG Load Stage To Failure |
|---|---|---|---|
| 1 | A | ZDDP | 9 |
| 2 | B | Phosphate A | 11 |
| 3 | B | Phosphate B | 11 |
| 4 | B | Phosphate C | 11 |
| 5 | B | Phosphate D | 10 |
| 6 | B | Phosphate E | 9 |

Referring to Table 1, it can be seen that all of the tested cyclic phosphates are at least as good as ZDDP with respect to anti-wear and in most instances are significantly better.

EXAMPLE 8

Part A

This example illustrates the effects of cyclic Phosphate B on friction modification.

Accordingly, an ATF base fluid, designated Base Fluid C was formulated containing conventional amounts of a borated ashless dispersant, seal swell additive, antioxidant, and V.I. improver.

Part B

To a sample of Base Fluid C was added 0.5 vol. % of Phosphate B and the resulting formulation designated Formulation G.

Part C

To another sample of Base Fluid C was added 0.1 vol. % of a $C_{12}$ alkyl substituted overbased sulfurized calcium phenate derived by reaction of the sulfurized substituted phenate and calcium hydroxide subsequently neutralized with $CO_2$ to a TBN of 250 (designated herein as Ca-Phenate A). The resulting formulation is designated Formulation H.

Part D

To another sample of Base Fluid C was added 0.1 vol. % of the Ca-Phenate A of Part C, and 0.5 vol. % of Phosphate B. The resulting formulation is designated Formulation I.

Part E

Formulations G to I were then tested in accordance with a Modified SAE No. 2 Friction Test.

The Modified SAE No.2 Friction Test

This test uses a SAE No.2 type Friction Machine operated successfully for 200 cycles wherein no unusual clutch plate wear or composition-face plate flaking occurs. The test is conducted in a continuous series of 20 second cycles, each cycle consisting of three phases as follows: Phase I (10 seconds)—motor on at speed of 3,600 rpm, clutch plates disengaged; Phase II (5 seconds)—motor off, clutch plates engaged; and Phase III (5 seconds)—motor off, clutch released. One-hundred and fifty cycles are repeated using 16,500 ft./lbs. of flywheel torque at 40 psi. of applied clutch pressure, followed by 50 cycles repeated using 16,500 ft./lbs. of flywheel torque at 60 psi. of applied clutch pressure. During the clutch engagement, friction torque is recorded as a function of time as the motor speed declines from 3600 rpm to 0. From the torque traces, the dynamic torque ($T_{1800}$) is determined midway between the start and end of clutch engagement (i.e. at a motor speed of 1800 rpm), as well as the torque at 200 rpm ($T_{200}$). The amount of time in seconds in phase II it takes for the motor speed to go from 3600 to 0 rpm is referred to as the lock-up time. The torque ratio of the oil formulation is then determined from ($T_{200}/T_{1800}$). The data reported herein at Table 2 is derived from the 200th cycle.

TABLE 2

| Run No. | Base Fluid Type | Formulation Type | Phosphate B (Vol. %) | Ca—Phenate A (Vol. %) | $T_{200}/T_{1800}$* |
|---|---|---|---|---|---|
| 7 | C | G | 0.5 | 0 | 0.98 |
| 8 | C | H | 0 | 0.1 | 1.14 |
| 9 | C | I | 0.5 | 0.1 | 1.01 |

*$T_{1800}$ for all runs was greater than 130 N.m.

Referring to Table 2, it can be seen from Run 8 that in the absence of Phosphate B, the friction modification property of $T_{200}/T_{1800}$ is well above 1. It is further concluded from Run 8 that Ca-Phenate A has no friction properties of its own. When Phosphate B is added to the formulation, the $T_{200}/T_{1800}$ is observed to be 0.98 which is entirely acceptable. This ratio increased only slightly in the additional presence of Ca-Phenate A.

EXAMPLE 9

This example illustrates the friction durability properties of the overbased sulfurized Ca-Phenate of the present invention.

Part A

Accordingly, an ATF base fluid, designated herein as Base Fluid D was formulated with conventional amounts of borated ashless dispersant, seal swell additive, antioxidant, V.I. improver and 0.1 vol. % of Friction Modifier A from Example 6.

Part B

To a sample of Base Fluid D was added 0.5 vol. % of Phosphate B. The resulting formulation is designated Formulation J.

Part C

To another sample of Base Fluid D was added 0.5 vol. % of Phosphate B and 0.1 vol. % of Ca-Phenate A of Part C of Example 8. The resulting formulation is designated Formulation K.

Part D

Formulations J and K were then tested in the High-Energy, Friction Characteristics and Durability Test (HEFCAD) described in Dexron II ® Specification GM6137-M Published by GMC Engineering Staff, Engineering Standards Section. This test is similar to the modified SAE No. 2 test described above, except that it is run for about 18,000 cycles (i.e. 100 hrs.) instead of only 200.

This test uses a SAE No. 2 Friction Machine operated successfully for 100 hours wherein no unusual clutch plate wear or composition-face plate flaking occurs. After a break-in period of 24 hours, the test is conducted in a continuous series of 20 second cycles, each cycle consisting of three phases as described in connection with the modified SAE-2 friction test. The cycles are repeated for 75 hours after the break-in (i.e. a total of 18,000 cycles) or until failure. One difference between the modified SAE-2 test and the HEFCAD is that the primary friction characteristic is determined by subtracting the Static Torque ($T_D$) from the midpoint dynamic torque ($T_D$). The static torque in the HEFCAD procedure is measured at an engine speed (rpm) at which the slope of the torque curve approaches infinity, e.g. between 20 and about 0 rpm. The dynamic torque ($T_D$) is measured midway between the start and end of clutch engagement, i.e. at 1800 rpm. Data is reported at various stages over the life of the test as indicated by "Test hour" at Table 3. The torque differential ($T_O - T_D$) not only expresses the primary friction characteristic but its change over the duration of the test reflects friction stability.

The results of the HEFCAD test for Formulations J and K are summarized at Table 3.

TABLE 3

| Run No. | Base Fluid Type | Formulation Type | Phosphate B (Vol. %) | Friction Modifier A (Vol. %) | Ca—Phenate-A (Vol. %) | Test Hour | $T_D$ | $T_O - T_D$ | Net Change in ($T_O - T_D$) Over 100 Hr. | Lock-up Time (Sec.) |
|---|---|---|---|---|---|---|---|---|---|---|
| 10 | D | J | 0.5 | 0.1 | 0 | 1 | N/R | −1 | N/A | N/R |
| 11 | D | J | 0.5 | 0.1 | 0 | 24 | N/R | +1 | N/A | N/R |
| 12 | D | J | 0.5 | 0.1 | 0 | 30 | N/R | +3 | N/A | N/R |
| 13 | D | J | 0.5 | 0.1 | 0 | 50 | N/R | +5 | N/A | N/R |
| 14 | D | J | 0.5 | 0.1 | 0 | 75 | N/R | +5 | N/A | N/R |
| 15 | D | J | 0.5 | 0.1 | 0 | 100 | 138 | +7 | +8 | .63 |
| 16 | D | K | 0.5 | 0.1 | 0.1 | 1 | N/R | −5 | N/A | N/R |
| 17 | D | K | 0.5 | 0.1 | 0.1 | 24 | N/R | −6 | N/A | N/R |
| 18 | D | K | 0.5 | 0.1 | 0.1 | 30 | N/R | −8 | N/A | N/R |
| 19 | D | K | 0.5 | 0.1 | 0.1 | 50 | N/R | −5 | N/A | N/R |
| 20 | D | K | 0.5 | 0.1 | 0.1 | 75 | N/R | −4 | N/A | N/R |

TABLE 3-continued

| Run No. | Base Fluid Type | Formulation Type | Phosphate B (Vol. %) | Friction Modifier A (Vol. %) | Ca—Phenate-A (Vol. %) | Test Hour | $T_D$ | $T_O - T_D$ | Net Change in $(T_O - T_D)$ Over 100 Hr. | Lock-up Time (Sec.) |
|---|---|---|---|---|---|---|---|---|---|---|
| 21 | D | K | 0.5 | 0.1 | 0.1 | 100 | 148 | −8 | −3 | .61 |

N/R = Not reported
N/A = Not applicable

As may be seen from Table 3, Formulation J in the absence of a friction stability promoter, yields a net change in torque differential over the life of the test (100 hrs.) of +8 with a final torque differential of +7. As indicated above, the more positive the torque differential the harsher the shifting. Moreover, harsh shifting is considerably more undesirable and pronounced with each incremental increase of $T_O-T_D$ above zero, than the associated potential increase in slippage for each incremental decrease in $T_O-T_D$ below zero. Thus, the overbased Ca phenate results in a considerable improvement in friction stability with a net change of −3 and the $T_D-T_O$ never exceeds zero for the life of the test.

EXAMPLE 10

This example is intended to illustrate the inter-relationship of Breakaway Static Torque ratio ($T_S/T_D$) and friction modification ($T_O/T_D$) on the amount of friction modifier and the ability to reduce friction modifier by employing the cyclic phosphate as a supplemental friction modifier and an anti-wear additive.

Part A

An ATF base fluid was formulated, designated Base Fluid E, containing conventional amounts of borated dispersant, seal swell additive, antioxidant, and V.I. improver.

Part B

To the Base Fluid E was added 0.15 vol. % of Friction Modifier A and 0.5 vol. % of Phosphate B. the resulting formulation is designated Formulation L.

Part C

To the Base Fluid E was added 0.23 vol. % of ZDDP; 0.1 vol. % Ca-Phenate A, and 0.3 vol. % of a copper corrosion inhibitor necessitated by the presence of ZDDP. The resulting base fluid is designated Base Fluid E'. To three different samples of Base Fluid E' was added a different amount of Friction Modifier A to make the following formulations as follows:

TABLE 4

| Base Fluid | + | Friction Modifier A (Vol. %) | = | Formulation Type |
|---|---|---|---|---|
| E' | | 0.1 | | M |
| E' | | 0.25 | | N |
| E' | | 0.30 | | O |

Part D

Formulations L to O were then tested according to a Toyota Friction Test. This test is similar to the Modified SAE No. 2 Friction Test but is run for 3,000 cycles and using 15,300 ft. lbs. of flywheel torque at 32 psi clutch pressure. The results are summarized at Table 5. The data reported is taken from the 3,000th cycle.

In addition to determining midpoint dynamic torque $T_D$ (at 1800 rpm) and the torque ratio ($T_O/T_D$), the breakaway static torque ($T_S$) is also determined. This is achieved by rotating the composition plates at 2 to 3 rpm under a load of 40 psi. while locking the steel reaction plates and preventing them from rotating. The torque is then measured until slippage occurs. The maximum torque observed is recorded as $T_S$. From $T_S$ is determined the Breakaway Static Torque ratio ($T_S/T_D$) which value is reported at Table 5.

The breakaway static torque ratio expresses the ability of the transmission to resist slippage; the lower the ratio the higher the slippage.

TABLE 5

| Run No. | Base Fluid Type | Formulation Type | Phosphate B (Vol. %) | Friction Modifier A (Vol. %) | Ca—Phenate-A (Vol. %) | $T_O$ | $T_D$ | $T_O/T_D$ | $T_S$ | $T_S/T_D$ |
|---|---|---|---|---|---|---|---|---|---|---|
| 22 | E | L | 0.5 | 0.15 | 0 | 174.6 | 173 | 1.01 | 163.9 | 0.95 |
| 23 | E' | M | 0 | 0.1 | 0.1 | 182.9 | 163.9 | 1.12 | 184 | 1.12 |
| 24 | E' | N | 0 | 0.25 | 0.1 | 161.2 | 166 | 0.97 | 150.6 | 0.91 |
| 25 | E' | O | 0 | 0.30 | 0.1 | 160 | 167 | 0.96 | 140 | 0.87 |
| 26 | E' - Extrapolated From Plot of Runs 23 to 25 | | | 0.15 | 0.1 | | 175.8 | 1.05 | | 0.93 |

Base Fluid E' = Base Fluid E + 0.23 Vol. % ZDDP, 0.1 Vol. % Ca—Phenate A, and 0.3 Vol. % of a copper corrosion inhibitor.

Referring to Table 5, it can be seen from Runs 23 to 25 that as the friction modifier concentration increases, the torque ratio $T_O/T_D$ improves to less than 1 but at the same time the breakaway static torque ratio $T_S/T_D$ deteriorates. Run 26 provides data obtained from extrapolation of plots of Runs 23 to 25 at a friction modifier concentration of 0.15. In contrast, the use of Phosphate B in Run 22 produces a $T_O/T_D$ of 1.01 compared to an expected value of 1.05 for Run 26, but also shows a $T_S/T_D$ of 0.95 which is better than the expected value of 0.93 for Run 26.

EXAMPLE 11

This example illustrates the anti-oxidation properties of the cyclic phosphate of the present invention.

Part A

An ATF base fluid, designated Base Fluid F, was formulated containing conventional amounts of a borated ashless dispersant, antioxidant, seal swell additive, I.V. improver and friction modifier.

Part B

To Base Fluid F was added 0.5 vol. % of Phosphate A and the resulting formulation designated Formulation P.

Part C

To another sample of Base Fluid F was added 0.5 vol. % of Phosphate B and the resulting formulation designated Formulation Q.

Part D

Base Fluid F, and Formulations P and Q were then tested by the Laboratory Multiple Oxidation Test (LMOT). In this test, 50 ml of test fluid with 2.0 g of iron filings and 0.5 g of a 1% solution of copper naphthenate is heated to 150° C. and 25 ml air per minute is passed through the sample. Daily samples are taken and the number of days for visible sludge to appear on blotter paper is recorded.

The results are summarized at Table 6.

TABLE 6

|  | Days to Failure |
| --- | --- |
| Base Fluid F | 5 |
| Formulation P (Phosphate A) | 16 |
| Formulation Q (Phosphate B) | 11 |

EXAMPLE 12

This example further illustrates the anti-oxidant properties of the cyclic phosphates of the present invention in accordance with the Turbo Hydromatic Oxidation Test (THOT).

Part A

An ATF base fluid, designated Base Fluid G was formulated using conventional amounts of borated ashless dispersant, antioxidant, seal swell additive, V.I. improver, Friction Modifier A (0.4 vol. %) and 0.5 vol. % of Phosphate B to form Formulation R.

Part B

The THOT measures the oxidation-stability of the fluid and is a standard test developed by General Motors Corp. described in General Motors Publication RLSP73-2, entitled DEXRON® II Specification GM 6137-M, Published by GMC Engineering Staff, Engineering Standards Section. To pass this test, a number of minimum requirements must be achieved. The results of the THOT on Formulation P are summarized as follows at Table 7.

TABLE 7

| Sludge | None |
| --- | --- |
| Used Oil Analyses | |
| Viscosity, cst. @ 100° C. | 5.9 |
| Total Acid No. Increase | 0.32 |
| % Pentene Insolubles | 0.02 |
| Carbonyl Group Absorbance | 0.18 |

The above results are considered excellent for an ATF.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A cyclic phosphate represented by the structural formula:

$$R-(S)_n-(R_1-O)_{n'}-P\begin{matrix}O\\\|\end{matrix}\begin{matrix}X-R_2\\X'-R_3\end{matrix}Y \bigg)_{n''} \qquad (I)$$

wherein R can represent alkyl, alkenyl, cycloalkyl, aralkyl, alkaryl; n is a number which can vary from 1 to about 3, $R_1$ is alkylene, n' is a number which can vary from about 1 to about 12; X' which may be the same or different can independently represent —O—, —NH— or —S—; $R_2$ and $R_3$ which may be the same or different can independently represent substituted or unsubstituted alkylene; n'' can represent the number 0 or 1; and Y can represent —O—, —NH—, —S—, —S—S—, or —CH$_2$— when n'' is 1; said $R_2$ and $R_3$ being joined together and constituting part of a cyclic hetero ring structure when n'' is 0.

2. The cyclic phosphate of claim 1 wherein in Formula I, R can represent about $C_6$ to about $C_{30}$ alkyl, $C_6$ to about $C_{30}$ alkenyl, n is 1, $R_1$ represents $C_1$ to about $C_4$ alkylene, and n' can vary from about 2 to about 6.

3. The cyclic phosphate of claim 2, wherein $R_2$ and $R_3$ are unsubstituted and independently represent $C_1$ to about $C_3$ alkylene.

4. The cyclic phosphate of claim 2, wherein $R_2$ and $R_3$ independently represent substituted $C_1$ to about $C_3$ alkylene wherein said substituents are independently selected from the group consisting of alkyl, cycloalkyl, aryl, aralkyl, alkaryl, alkylthiomethylalkyl, arylthiomethylalkyl, alkylthioaralkyl, alkylthioalkaryl, alkylthiocycloalkyl, and hydroxyalkyl.

5. The cyclic phosphate of claim 1, wherein X and X' are —O—, n'' is 1, Y is —O—, and $R_2$ and $R_3$ are ethylene.

6. The cyclic phosphate of claim 1, wherein X and X' are —O—, n'' is 1, Y is —S— or —S—S—, and $R_2$ and $R_3$ are ethylene.

7. The cyclic phosphate of claim 1, wherein X is —O—, X' is —S—, n'' is 0, and $R_2$ and $R_3$ are independently selected from the group consisting of methylene and ethylene.

8. The cyclic phosphate of claim 1, wherein X and X' are —O—, n'' is 0, and $R_2$ and $R_3$ are methylene.

9. The cyclic phosphate of any one of claims 1 to 8, wherein n is 1, R is about $C_{12}$ to about $C_{18}$ straight chain alkyl or alkenyl, $R_1$ is about $C_1$ to about $C_3$ alkylene, and n' is from about 2 to about 4.

10. An oleaginous composition comprising an oleaginous material selected from the group consisting of fuels and lubricating oil, and at least one cyclic phosphate according to claim 1 dissolved in said oleaginous material.

11. The oleaginous composition of claim 10, wherein the oleaginous material is a fuel oil.

12. The oleaginous composition of claim 10, wherein the oleaginous material is a lubricating oil.

13. The oleaginous composition of claim 11, wherein the cyclic phosphate is present in an amount of from about 8 to about 400 ppm. parts of the composition.

14. The oleaginous composition of claim 12, wherein the cyclic phosphate is present in an amount of from about 0.05 to about 1.5 wt. %, based on the weight of the composition.

15. The oleaginous composition of claim 10, wherein the cyclic phosphate is according to claim 2.

16. The oleaginous composition of claim 10, wherein the cyclic phosphate is according to claim 3.

17. The oleaginous composition of claim 10, wherein the cyclic phosphate is according to claim 4.

18. The oleaginous composition of claim 10, wherein the cyclic phosphate is according to claim 5.

19. The oleaginous composition of claim 10, wherein the cyclic phosphate is according to claim 6.

20. The oleaginous composition of claim 10, wherein the cyclic phosphate is according to claim 7.

21. The oleaginous composition of claim 10, wherein the cyclic phosphate is according to claim 8.

22. The oleaginous composition of claim 10, wherein the cyclic phosphate is according to claim 9.

23. The oleaginous composition of claim 11, wherein the cyclic phosphate is according to claim 9.

24. An oil soluble reaction product of:
(1) an organo phosphorus oxydichloride represented by formula:

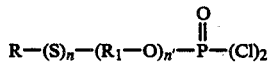

wherein R can represent alkyl, alkenyl, cycloalkyl, aralkyl, and alkaryl; n is a number which can vary from about 1 to about 12; and
(2) a cyclizing agent represented by the formula:

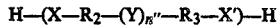

wherein X and X' which may be the same or different can independently represent —O—, —NH—, —S—; R2 and R3 which may be the same or different can independently represent substituted or unsubstituted alkylene; n" can represent the number 0 or 1; and Y can represent —O—, —NH—, —S—, —S—S—, or —CH2— when n" is 1; wherein said reactive components 1 and 2 are reacted at about a 1:1 molar ratio and under reaction conditions effective to produce said product, and liberated HCl is removed from the product produced thereby.

25. The reaction product of claim 24, wherein in reactive component (1) R represents $C_6$ to about $C_{30}$ alkyl, n is 1, $R_1$ represents $C_1$ to about $C_4$ alkylene, and n' can vary from about 2 to about 6.

26. The reaction product of claim 24, wherein in reactive component (2) $R_2$ and $R_3$ are unsubstituted and independently represent $C_1$ to about $C_3$ alkylene.

27. The reaction product of claim 25, wherein in reactive component (2) $R_2$ and $R_3$ independently represent substituted $C_1$ to about $C_3$ alkylene wherein said substituents are independently selected from the group consisting of alkyl, cycloalkyl, aryl, aralkyl, alkaryl, alkylthiomethylalkyl, arylthiomethylalkyl, alkylthioaralkyl, alkylthioalkaryl, alkylthiocycloalkyl, and hydroxyalkyl.

28. The reaction product of claim 24, wherein in reactive component (2) X and X' are —O—, n" is 1, Y is —O—, —S—, or —S—S—, and $R_2$ and $R_3$ are ethylene.

29. The reaction product of claim 24, wherein in reactive component (2) X is —S—, X' is —O—, n" is 0, and $R_2$ and $R_3$ are independently selected from the group consisting of methylene and ethylene.

30. The reaction product of claim 24, wherein in reactive component (2), X and X' are —O—, n" is 0, and $R_2$ and $R_3$ are each methylene.

31. The reaction product of any one of claims 24 to 30, wherein in reactive component (1), n is 1, R is about $C_{12}$ to about $C_{18}$ straight chain alkyl or alkenyl, $R_1$ is about $C_1$ to about $C_3$ alkylene, and n' is from about 2 to about 4.

32. A lubricating oil composition comprising a lubricating oil and a cyclic phosphate according to claim 1.

33. The lubricating oil composition of claim 32, wherein said cyclic phosphate is according to claim 2.

34. The lubricating oil composition of claim 32, wherein said cyclic phosphate is according to claim 3.

35. The lubricating oil composition of claim 32, wherein the cyclic phosphate is according to claim 4.

36. The lubricating oil composition of claim 32, wherein the cyclic phosphate is according to claim 5.

37. The lubricating oil composition of claim 32, wherein the cyclic phosphate is according to claim 6.

38. The lubricating oil composition of claim 32, wherein the cyclic phosphate is according to claim 7.

39. The lubricating oil composition of claim 32, wherein the cyclic phosphate is according to claim 8.

40. The lubricating oil composition of claim 32, wherein the cyclic phosphate is according to claim 9.

41. The lubricating oil composition of claim 32, which comprises a major amount of lubricating oil and a minor amount of said cyclic phosphate.

42. The lubricating oil composition of claim 41, wherein said cyclic phosphate is present in said composition in an amount of from about 0.1 to about 1 wt. %, based on the composition weight.

43. The lubricating oil composition of claim 41, wherein said lubricating oil is a mineral oil.

44. The lubricating oil composition of claim 32, wherein said cyclic phosphate is present in said composition in an amount effective to improve at least one of the properties of anti-wear, anti-oxidation and friction modification possessed by said composition relative to the absence of said phosphate.

45. The lubricating oil composition of claim 32, which has been adapted for use as a power transmitting fluid.

46. The lubricating oil composition of claim 45, wherein said power transmitting fluid is an automatic transmission fluid.

47. A lubricating oil composition adaptable for use as an automatic transmission fluid which comprises mineral oil and an amount of a cyclic phosphate effective to impart at least one of the properties of anti-wear, friction modification, and anti-oxidation, to said fluid, said cyclic phosphate being represented by the formula:

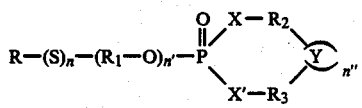

wherein R represents alkyl, alkenyl, cycloalkyl, aralkyl, and alkaryl; n is a number which can vary from 1 to about 3, $R_1$ is alkylene, n' is a number which can vary from about 1 to about 12; X and X' which may be the same or different can independently represent —O—, —NH— or —S—; $R_2$ and $R_3$ which may be the same or different can independently represent substituted or unsubstituted alkylene; n" can represent the number 0 or 1; and Y can represent —O—, —NH—, —S—, —S—S—, or —CH$_2$— when n" is 1; said $R_2$ and $R_3$ being joined together and constituting part of a cyclic hetero ring structure when n" is 0.

48. The lubricating oil composition of claim 47, wherein in said cyclic phosphate of Formula (I), R can represent about $C_6$ to about $C_{30}$ alkyl, about $C_6$ to about $C_{30}$ alkenyl, n is 1, $R_1$ represents $C_1$ to about $C_4$ alkylene, and n' can vary from about 2 to about 6.

49. The lubricating oil composition of claim 47, wherein in said cyclic phosphate $R_2$ and $R_3$ are unsubstituted and independently represent $C_1$ to about $C_3$ alkylene.

50. The lubricating oil composition of claim 47, wherein in said cyclic phosphate $R_2$ and $R_3$ independently represent substituted $C_1$ to about $C_3$ alkylene, wherein said substituents are independently selected from the group consisting of alkyl, cycloalkyl, aryl, aralkyl, alkaryl, alkylthiomethylalkyl, arylthiomethylalkyl, alkylthioaralkyl, alkylthioalkaryl, alkylthiocycloalkyl, and hydroxyalkyl.

51. The lubricating oil composition of claim 47, wherein in said cyclic phosphate X and X' are —O—, n" is 1, Y is —O—, and $R_2$ and $R_3$ are ethylene.

52. The lubricating oil composition of claim 47, wherein in said cyclic phosphate X and X' are —O—, n" is 1, Y is —S—, and $R_2$ and $R_3$ are ethylene.

53. The lubricating oil composition of claim 47, wherein in said cyclic phosphate X is —O—, X' is —S—, n" is 0, and $R_2$ and $R_3$ are independently selected from the group consisting of methylene and ethylene.

54. The lubricating oil composition of claim 47, wherein in said cyclic phosphate X and X' are —O—, n" is 0, and $R_2$ and $R_3$ are methylene.

55. The lubricating oil composition of any one of claims 47 to 54, wherein in said cyclic phosphate n is 1, R is about $C_{12}$ to about $C_{18}$ straight chain alkyl or alkenyl, $R_1$ is about $C_1$ to $C_3$ alkylene, and n' is from about 2 to about 4.

56. The lubricating oil composition of claim 55, wherein said composition additionally comprises:
(1) a friction modifying amount of at least one succinate ester compound or metal salt thereof, said succinate ester being the reaction product of:
(A) an alcohol represented by the structural formula:

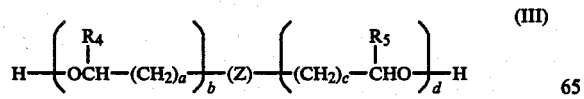

wherein $R_4$ and $R_5$ each independently can represent hydrogen or $C_1$ to $C_6$ alkyl; (a), (b), (c), and (d) each independently represent a number which can vary from 1 to about 3; and Z represents a linking group selected from —S—, —S—S—, —O—, and $NR_6$ wherein $R_6$ can represent hydrogen, $C_1$ to about $C_4$ alkyl, or $C_1$ to about $C_4$ monohydroxy substituted alkyl; and (B) from about 1 to about 2 moles per mole of alcohol of an acid or anhydride represented by the respective structural formulas:

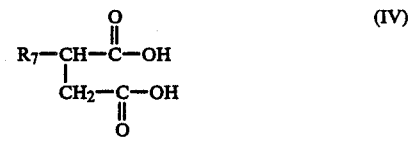

and

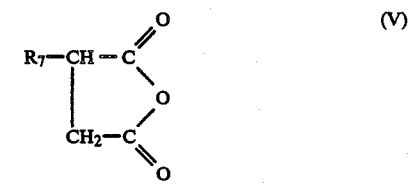

wherein $R_7$ is an aliphatic hydrocarbon group containing from about 12 to about 50 carbons; the metal of said succinate metal salt when employed being selected from the group consisting of Mg, Ca, Ba, Zn, N, Cu, Mo and mixtures thereof; and (2) a friction stability improving amount of at least one friction stability promoter selected from the group consisting of overbased: metal phenate, sulfurized metal phenate, metal sulfonate.

57. A lubricating oil composition adaptable for use as a power transmitting fluid which comprises a lubricating oil having dissolved therein at least one cyclic phosphate, at least one succinate ester or metal salt thereof, and at least one overbased friction stability promoter wherein:

(1) said cyclic phosphate is represented by the structural formula:

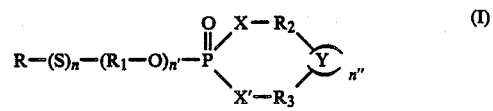

wherein R can represent alkyl, alkenyl, cycloalkyl, aralkyl, and alkaryl; n is a number which can vary from 1 to about 3, $R_1$ is alkylene, n' is a number which can vary from about 1 to about 12; X and X' which may be the same or different can independently represent —O—, —NH— or —S—; $R_2$ and $R_3$ which may be the same or different can independently represent substituted or unsubstituted alkylene; n" can represent the number 0 or 1 and Y can represent —O—, —NH—, —S—, —S—S—, or —CH$_2$— when n" is 1; said $R_2$ and $R_3$ being joined together and constituting part of a cyclic hetero ring structure when n" is 0;

(2) said succinate ester is the reaction product of:
(A) an alcohol represented by the structural formula:

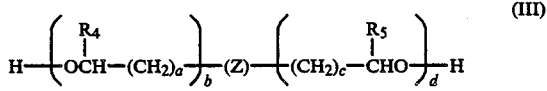

wherein R$_4$ and R$_5$ each independently can represent hydrogen or C$_1$ to C$_6$ alkyl; (a), (b), (c), and (d) each independently represent a number which can vary from 1 to about 3; and Z represents a linking group selected from —S—, —S—S—, —O—, and NR$_6$ wherein R$_6$ can represent hydrogen, C$_1$ to about C$_4$ alkyl, or C$_1$ to about C$_4$ monohydroxy substituted alkyl; and (B) from about 1 to about 2 moles per mole of alcohol of an acid or anhydride represented by the respective structural formulas:

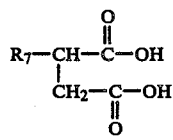

and

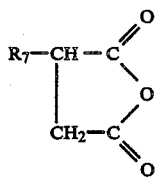

wherein R$_7$ is an aliphatic hydrocarbon group containing from about 12 to about 50 carbons; said metal of the metal salt when employed being selected from the group consisting of Mg, Ca, Ba, Zn, Ni, Cu, Mo and mixtures thereof; and (3) said overbased friction stability promoter is selected from the group consisting of (a) metal phenate derived from the reaction of a phenol or substituted phenol and an alkali or alkaline earth metal base; (b) sulfurized metal phenate; (c) metal sulfonate derived from the reaction of at least one aliphatic or aromatic sulfonic acid with an alkali or alkaline earth metal base; and (d) mixtures thereof.

58. The lubricating oil composition of claim 57, wherein:

(1) in said cyclic phosphate of Formula (I), n is 1, R can represent C$_{12}$ to C$_{18}$ straight chain alkyl or C$_{12}$ to C$_{18}$ straight chain alkenyl; R$_1$ can represent C$_2$ to C$_4$ alkylene, n' can vary from about 1 to about 6; R$_2$ and R$_3$ are unsubstituted C$_1$ to C$_2$ alkylene;

(2) a succinate ester is employed as the second component, and in said alcohol of Formula (III), (a), (b), (c) and (d) are 1, R$_4$ and R$_5$ are independently hydrogen, methyl or ethyl, and in the acid or anhydride of Formula's IV and V, R$_7$ is a C$_{16}$ to C$_{30}$ straight chain aliphatic group; and (3) said friction stability promoter is a sulfurized metal phenate having a TBN of from about 30 to about 450, and is derived from a mono-C$_6$ to about C$_{20}$ straight chain alkyl substituted phenol and an alkaline earth metal base.

59. The lubricating oil composition of claim 58, wherein:

(1) in said cyclic phosphate of Formula (I), n' can vary from about 2 to about 4, X and X' are independently —O—, or —S—, R$_1$ and R$_2$ are C$_1$ to C$_2$ alkylene, n" is 1, and Y is —O—, —S—, or —S—S—;

(2) in said acid or anhydride of Formulas (IV) and (V), R$_7$ contains from 18 to 22 carbons; and (3) the alkaline earth metal of said metal base is selected from the group consisting of Ca or Mg.

60. The lubricating oil composition of claim 59, wherein in Formula (I), X and X' are —O—.

61. A process for improving at least one of the properties of anti-wear, friction modification, and anti-oxidation of an oleaginous composition which comprises admixing at least an amount effective to improve at least one of said properties of a cyclic phosphate with an oleaginous material selected from the group consisting of fuels and lubricating oils, said cyclic phosphate being represented by the formula:

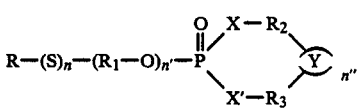

wherein R can represent alkyl, alkenyl, cycloalkyl, aralkyl, and alkaryl; n is a number which can vary from 1 to about 3, R$_1$ is alkylene, n' is a number which can vary from about 1 to about 12; X and X' which may be the same or different can independently represent —O—, —NH—, or —S—; R$_2$ and R$_3$ which may be the same or different can independently represent substituted or unsubstituted alkylene; n" can represent the number 0 or 1; and Y can represent —O—, —NH—, —S—, —S—S—, or —CH$_2$— when n' is 1; and said R$_2$ and R$_3$ being joined together and constituting part of a cyclic hetero ring structure when n" is O.

62. A process for improving the friction stability of a lubricating oil composition which when adapted for use as an automatic transmission fluid contains a friction modifying effective amount of a friction modifier comprising a cyclic phosphate represented by the formula:

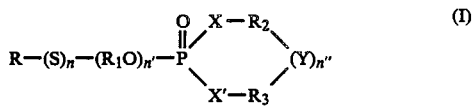

wherein R represents alkyl, alkenyl, cycloalkyl, aralkyl, and alkaryl; n is a number which can vary from 1 to about 3, R$_1$ is alkylene, n' is a number which can vary from about 1 to about 12; X and X' which may be the same or different independently represent —O—, —NH—, or —S—' R$_2$ and R$_3$ which may be the same or different independently represent substituted or unsubstituted alkylene; n" represents the number 0 or 1; and Y represents —O—, —NH—, —S—, —S—S— or —CH$_2$ when n' is 1; and said R$_2$ and R$_3$ being joined together and constituting part of a cyclic hetero ring structure when n" is o; which comprises adding to said lubricating oil composition a friction stability improving effective amount of at least one overbased friction stability promoter selected from the group consisting of (a) metal phenate, (b) sulfurized metal phenate, and (c) metal sulfonate, wherein said metal is selected from the group consisting of alkali metal, alkaline earth metal and mixtures thereof.

63. The process of claim 62 wherein said friction stability promoter is a sulfurized metal phenate having a TBN of from about 30 to about 450.

64. The process of claim 62 wherein said friction stability promoter is added to said lubricating oil composition in an amount sufficient to achieve a weight ratio of friction modifier to friction stability promoter of from about 1:1 to about 10:1.

65. The process of claim 63 wherein said sulfurized metal phenate is derived from the reaction of a substituted phenol and a calcium or magnesium base; said substituent being a $C_6$ to about $C_{20}$ straight chain alkyl group.

66. An oleaginous composition comprising an oleaginous material selected from the group consisting of fuels and lubricating oil, and at least an amount effective to impart to said oleaginous material at least one of enhanced anti-wear, anti-oxident or friction modification properties of at least one cyclic phosphate according to claim 1.

67. The oleaginous composition of claim 66 wherein the oleaginous material is a fuel oil.

68. The oleaginous composition of claim 66 wherein the oleaginous material is a lubricating oil.

69. The oleaginous composition of claim 66 wherein the cyclic phosphate is according to claim 2.

70. The oleaginous composition of claim 66 wherein the cyclic phosphate is according to claim 3.

71. The oleaginous composition of claim 66 wherein the cyclic phosphate is according to claim 4.

72. The oleaginous composition of claim 66 wherein the cyclic phosphate is according to claim 5.

73. The oleaginous composition of claim 66 wherein the cyclic phosphate is according to claim 6.

74. The oleaginous composition of claim 66 wherein the cyclic phosphate is according to claim 7.

75. The oleaginous composition of claim 66 wherein the cyclic phosphate is according to claim 8.

76. The oleaginous composition of claim 66 wherein the cyclic phosphate is according to claim 9.

77. A lubricating oil composition comprising a lubricating oil and at least an amount effective to impart to said lubricating oil at least one of enhanced anti-wear, anti-oxidant or friction modification properties of a cyclic phosphate according to claim 1.

78. A lubricating oil composition comprising a lubricating oil and at least an amount effective to impart to said lubricating oil at least one of enhanced anti-wear, anti-oxidant or friction modification properties of a cyclic phosphate according to claim 2.

79. A lubricating oil composition comprising a lubricating oil and at least an amount effective to impart to said lubricating oil at least one of enhanced anti-wear, anti-oxidant or friction modification properties of a cyclic phosphate according to claim 3.

80. A lubricating oil composition comprising a lubricating oil and at least an amount effective to impart to said lubricating oil at least one of enhanced anti-wear, anti-oxidant or friction modification properties of a cyclic phosphate according to claim 4.

81. A lubricating oil composition comprising a lubricating oil and at least an amount effective to impart to said lubricating oil at least one of enhanced anti-wear, anti-oxidant or friction modification properties of a cyclic phosphate according to claim 5.

82. A lubricating oil composition comprising a lubricating oil and at least an amount effective to impart to said lubricating oil at least one of enhanced anti-wear, anti-oxidant or friction modification properties of a cyclic phosphate according to claim 6.

83. A lubricating oil composition comprising a lubricating oil and at least an amount effective to impart to said lubricating oil at least one of enhanced anti-wear, anti-oxidant or friction modification properties of a cyclic phosphate according to claim 7.

84. A lubricating oil composition comprising a lubricating oil and at least an amount effective to impart to said lubricating oil at least one of enhanced anti-wear, anti-oxidant or friction modification properties of a cyclic phosphate according to claim 8.

85. A lubricating oil composition comprising a lubricating oil and at least an amount effective to impart to said lubricating oil at least one of enhanced anti-wear, anti-oxidant or friction modification properties of a cyclic phosphate according to claim 9.

* * * * *